US011286282B2

(12) United States Patent
Haynes

(10) Patent No.: US 11,286,282 B2
(45) Date of Patent: Mar. 29, 2022

(54) METHODS OF DETECTION AND REMOVAL OF RHABDOVIRUSES FROM CELL LINES

(71) Applicant: TAKEDA VACCINES, INC., Cambridge, MA (US)

(72) Inventor: Joel R. Haynes, Cambridge, MA (US)

(73) Assignee: Takeda Vaccines, Inc., Cambridge, MA (US)

(*) Notice: Subject to any disclaimer, the term of this patent is extended or adjusted under 35 U.S.C. 154(b) by 0 days.

(21) Appl. No.: 16/662,784

(22) Filed: Oct. 24, 2019

(65) Prior Publication Data
US 2020/0190146 A1    Jun. 18, 2020

Related U.S. Application Data

(63) Continuation of application No. 15/026,719, filed as application No. PCT/US2014/059060 on Oct. 3, 2014, now Pat. No. 10,501,500.

(60) Provisional application No. 61/886,438, filed on Oct. 3, 2013.

(51) Int. Cl.
| | |
|---|---|
| C07K 14/005 | (2006.01) |
| C12N 7/00 | (2006.01) |
| C07K 1/14 | (2006.01) |
| C12Q 1/70 | (2006.01) |
| A61K 39/205 | (2006.01) |
| A61K 39/00 | (2006.01) |

(52) U.S. Cl.
CPC .......... *C07K 14/005* (2013.01); *A61K 39/205* (2013.01); *C07K 1/14* (2013.01); *C12N 7/00* (2013.01); *C12Q 1/701* (2013.01); *A61K 2039/5258* (2013.01); *C12N 2760/20021* (2013.01); *C12N 2760/20023* (2013.01); *C12N 2760/20034* (2013.01); *C12N 2760/20051* (2013.01); *C12N 2760/20052* (2013.01); *C12N 2770/16023* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,024,947 | A | 6/1991 | Inlow et al. |
| 7,955,603 | B2 | 6/2011 | Richardson et al. |
| 8,431,116 | B2 | 4/2013 | Richardson et al. |
| 8,481,693 | B2 | 7/2013 | Vedvick et al. |
| 8,841,120 | B2 | 9/2014 | Richardson et al. |
| 10,501,500 | B2 | 12/2019 | Haynes et al. |
| 2011/0182975 | A1 | 7/2011 | Richardson et al. |
| 2013/0273102 | A1 | 10/2013 | Richardson et al. |
| 2014/0004145 | A1 | 1/2014 | Taylor et al. |
| 2016/0244487 | A1 | 8/2016 | Haynes et al. |

FOREIGN PATENT DOCUMENTS

| | | |
|---|---|---|
| CN | 102605106 B | 9/2013 |
| JP | 2011-006489 A | 2/1991 |
| JP | H03-500602 T | 2/1991 |
| WO | WO 1989/001028 A1 | 2/1989 |
| WO | WO 2010/109920 A1 | 9/2010 |
| WO | WO 2015/051255 A1 | 4/2015 |

OTHER PUBLICATIONS

Staljanssens et al., 2011, Antihypertensive effect of insect cells: In vitro and in vivo evaluation, vol. 32, pp. 526-530.*
Mukherjee and Hanley, 2010, Research article RNA interference modulates replication of dengue virus in *Drosophila melanogaster* cells, vol. 10, No. 127.*
Liu et al., 2011, Chimeric severe acute respiratory syndrome coronavirus (SARS-CoV) S glycoprotein and influenza matrix 1 efficiently form virus-like particles (VLPs) that protect mice against challenge with SARS-CoV, Vaccine, vol. 29, pp. 6606-6613.*
Park et al., 2003, Enhanced Mucosal and Systemic Immune ResponsesFollowing Intravaginal Immunization With HumanPapillomavirus 16 L1 Virus-Like Particle Vaccine inThermosensitive Mucoadhesive Delivery Systems, Journal of Medical Virology, vol. 70, pp. 633-641.*
Goodman, et al., "Establishment and characterization of insect cell lines from 10 lepidopteran species". In Vitro Cell Dev Biol Anim. (Jun. 2001); 37(6): 367-373.
Grasela, et al., "Expression of the green fluorescent protein carried by Autographa californica multiple nucleopolyhedrovirus in insect cell lines". In Vitro Cell Dev Biol Anim. (Mar. 2000); 36(3): 205-210.
Office Action in Japanese Patent Application No. 2019-207576 dated Oct. 1, 2020, and English translation, 4 pages.
Office Action in Japanese Patent Application No. 2016-520073 dated Oct. 1, 2020, and English translation, 28 pages.
Office Action in Canadian Application No. 2,926,225 dated Sep. 9, 2020, 4 pages.
International Application No. PCT/US2014/059060, International Search Report and Written Opinion dated Jan. 29, 2015, 11 pages.
International Application No. PCT/US2014/059060, International Preliminary Report on Patentability dated Apr. 5, 2016, 8 pages.
EP Application No. 14850556.3, Extended European Search Report dated May 15, 2017, 6 pages.
Ammar, el-D., et al., "Cellular and molecular aspects of rhabdovirus interactions with insect and plant hosts." Annual Review of Entomology (2009); 54: 447-468.
Bock, J.O., et al., "Identification and partial characterization of Taastrup virus: a newly identified member species of the Mononegavirales." Virology (2004); 319(1): 49-59.

(Continued)

*Primary Examiner* — Benjamin P Blumel
(74) *Attorney, Agent, or Firm* — Cooley LLP

(57) ABSTRACT

The present disclosure relates to compositions, methods, mixtures, and kits for detecting the presence of, and for removing, a virus from a product produced in an insect cell. The disclosure also relates to proteins, peptides, polypeptides, drug substances, biological products, vaccine antigens, and virus-like particles that are produced in an insect cell and that are free or substantially free of a virus. The disclosure also relates to compositions, methods, assays, and kits for detecting a rhabdovirus in a sample.

8 Claims, 3 Drawing Sheets
Specification includes a Sequence Listing.

(56) References Cited

OTHER PUBLICATIONS

Database Embl [Online] Jun. 25, 2010 (Jun. 25, 2010), "Bombyx mori mRNA, done: bmnc30d11,3' end sequence, expressed in BmNPV-infected BmN cells.", retrieved from EBI accession No. EM_ST:FY063436 Database accession No. FY063436, 1 page.
FY063436 cDNA library from BmNPV-infected BmN cells Bombyx mori cDNA clone bmnc30d11 3', mRNA sequence, GenBank [online], 2011, 1 page, [retrieved on Jul. 31, 2018], URL<https://www.ncbi.nlm.nih.gov/nucest/299564197?sat=1&satkey=70069183>.
Hashimoto, Y., et al., "Complete study demonstrating the absence of rhabdovirus in a distinct Sf9 cell line." PLoS ONE (2017); 12(4): e0175633. https://doi.org/10.1371/journal.pone.0175633.
Herrero, S., et al., "Identification and recombinant expression of a novel chymotrypsin from Spodoptera exigua." Insect Biochem Mol Biol. (2005); 35(10): 1073-1082.
Jackson, A.O., et al. "Biology of plant rhabdoviruses." Annu. Rev. Phytopathol. (2005); 43: 623-660.
Japanese Patent Application No. 2016-520073, Office Action dated Aug. 6, 2018 with English translation, 12 pages.
Katsuma, et al., "Mass identification of transcriptional units expressed from the Bombyx mori nudeopolyhedrovirus genome." Journal of General Virology (2011); 92(Pt 1): 200-203.
Ma, H., et al., "Identification of a Novel Rhabdovirus in Spodoptera frugiperda Cell Lines." J. Virol. (2014); 88(12): 6576-6585.
Maghodia, Ajay B., et al., "Characterization of an Sf-rhabdovirus-negative Spodoptera frugiperda cell line as an alternative host for recombinant protein production in the baculovirus-insect cell system." Protein Expression and Purification (2016); 122: 45-55.
Miller, T.A., et al., "Rapid and sensitive reverse transcriptase-polymerase chain reaction based detection and differential diagnosis of fish pathogenic rhabdoviruses in organ samples and cultured cells". Disease of Aquatic Organisms (Sep. 11, 1998); 34(1): 13-20.
Office Action in Australian Patent Application No. 2014329403, dated Nov. 28, 2019, 6 pages.
Ojosnegros, S., et al., "Viral genome segmentation can result from a trade-off between genetic content and particle stability." PLoS Genet. (2011); 7(3):e1001344. doi: 10.1371/journal.pgen.1001344. Epub Mar. 17, 2011.
Schroeder, et al., "Host Range and Population Survey of Spodoptera frugiperda Rhabdovirus". J Virol. (Mar. 5, 2019); 93(6). pii: e02028-18, pp. 1-14. Print Mar. 15, 2019.
Vaughn, J.L., et al. "The establishment of two cell lines from the insect Spodoptera frugiperda (Lepidoptera; Noctuidae)." In Vitro Cellular & Developmental Biology-Plant (1977); 13(4): 213-217.
Walker, P.J, et al., "Rhabdovirus accessory genes." Virus Res. (2011); 162(1-2): 110-125.
Geisler and Jarvis, "Insect Cell Glycosylation Patterns in the Context of Biopharmaceuticals". Post-translational Modification of Protein Biopharmaceuticals (Edited by Gary Walsh) (2009); Ch. 7, pp. 165-191,45 pages, ISBN: 978-3-527-32074-5.
Rendić, et al., "The Glycosylation Capacity of Insect Cells". Croatica Chemica Acta (2008); CCACAA 81(1): 7-21.
Cérutti and Golay, "Lepidopteran cells, an alternative for the production of recombinant antibodies?" MAbs. (May 1, 2012); 4(3): 294-309.
Mauch, et al., "Baculovirus-Mediated Expression of Human 65 kDa and 67 kDa Glutamic Acid Decarboxylases in SF9 Insect Cells and Their Relevance in Diagnosis of Insulin-Dependent Diabetes Mellitus". The Journal of Biochemistry (Jun. 1993); 113 (6): 699-704.

* cited by examiner

METHODS OF DETECTION AND REMOVAL OF RHABDOVIRUSES FROM CELL LINES

CROSS-REFERENCE TO RELATED APPLICATIONS

This application is a Continuation of U.S. patent application Ser. No. 15/026,719, filed on Apr. 1, 2016, which is a national stage of International Patent Application No. PCT/US2014/059060, filed on Oct. 3, 2014, which claims the benefit of priority to U.S. Provisional Patent Application No. 61/886,438, filed on Oct. 3, 2013, the entire contents of each are incorporated by reference herein in their entireties for all purposes.

DESCRIPTION OF THE TEXT FILE SUBMITTED ELECTRONICALLY HEREWITH

The content of the text file submitted electronically herewith is incorporated herein by reference in its entirety: a computer readable format copy of the Sequence Listing (filename: LIGO_026_01US_SeqList_ST25.txt; date recorded: Oct. 21, 2019; file size 18 Kb).

BACKGROUND

Insect cells such as SF21 and SF9 cells are commonly used for protein expression, including for the production of therapeutic biological products for use in human disease. Insect cells are often used in conjunction with baculovirus expression systems. Such baculovirus-insect cell expression systems have been used for the production of biological products due to their ability to grow to high density and express sufficient levels of protein, and due to the fact that they can readily be adapted to large scale suspension cultures. It has long been thought that these cells are free of contaminating viruses, as a result of extensive testing.

There is a need in the art for insect cells that are free of contaminating viruses, for methods for determining if the insect cells are free of contaminating viruses, and for products produced from insect cells that are free of contaminating viruses and suitable for human therapies.

SUMMARY OF THE INVENTION

In one aspect, the present disclosure provides compositions, methods, assays, and kits for detecting contaminating agents in a sample. In some embodiments, the sample is a protein, peptide, drug substance, biological product, virus, vaccine antigen, or virus-like particle (VLP) preparation that is produced in or generated using an insect cell line. In some embodiments, the insect cell line is Sf9 or Sf21. In some embodiments, the contaminating agent is a virus or a portion of a viral genome. In some embodiments, the disclosure provides compositions, methods, assays, and kits for detection of a novel virus that is herein termed "Sf9 rhabdovirus." In one aspect, the present disclosure provides the nucleic acid sequence and other features of Sf9 rhabdovirus. In another aspect, the present disclosure provides compositions, methods, assays, and kits for determining if the Sf9 rhabdovirus, or Sf9 rhabdovirus nucleic acids or Sf9 rhabdovirus particles in a sample are capable of replication. In some embodiments, the present disclosure provides compositions, methods, assays, and kits for determining (i) if a sample contains detectable levels of SD rhabdovirus RNA, as measured by RT-PCR; (ii) if the Sf9 rhabdovirus RNA is present in nuclease resistant particles in the sample; and/or (iii) if the SD rhabdovirus RNA is capable of replication.

In one aspect, the present invention provides a method for detecting a virus comprising detecting a nucleic acid sequence comprising at least 25, at least 50, at least 100, at least 250, at least 500, at least 750, at least 1000, at least 1250, at least 1500, or at least 2000 contiguous nucleotides of SEQ ID NO: 1 or the reverse complement of SEQ ID NO: 1. In some embodiments, the method for detecting the virus disclosed herein comprises using one or more primers and one or more labeled probes in a PCR assay. In some embodiments, the probe is a labeled probe.

In some embodiments, the present disclosure provides a method for detecting a virus wherein the method has a sensitivity level of between about 1 molecule of RNA and about 50 molecules of RNA.

In one aspect, the present disclosure provides methods for removing a virus from a protein, peptide, drug substance, biological product, vaccine antigen, or virus-like particle (VLP) preparation, wherein the protein, peptide, drug substance, biological product, vaccine antigen, or VLP preparation is generated using or produced in an insect cell, and wherein the virus comprises a sequence having at least 50%, at least 55%, at least 60%, at least 65%, at least 70%, at least 75%, at least 80%, at least 85%, at least 90%, at least 95%, or at least 99% homology to SEQ ID NO: 1. In a further embodiment, the virus comprises a sequence according to SEQ ID NO: 1. In embodiments, the insect cell is an Sf9 cell or an Sf21 cell. In further embodiments, the SD cell is derived from the cell line deposited as ATCC CRL-1711.

In one aspect, the present disclosure provides a protein, peptide, drug substance, biological product, vaccine antigen, or VLP preparation produced in an insect cell, wherein the protein, peptide, drug substance, biological product, vaccine antigen, or VLP is substantially free of a virus comprising a nucleotide sequence having at least 50%, at least 55%, at least 60%, at least 65%, at least 70%, at least 75%, at least 80%, at least 85%, at least 90%, at least 95%, or at least 99% homology to SEQ ID NO: 1. In a further embodiment, the virus comprises a sequence according to SEQ ID NO: 1. In embodiments, the insect cell is an Sf9 cell or an Sf21 cell. In further embodiments, the Sf9 cell is derived from the cell line deposited as ATCC CRL-1711. The present invention also encompasses compositions comprising such substances and optionally combined with pharmaceutically acceptable carriers, as well as kits for detecting the presence or absence of the virus in such substances.

In one aspect, the present disclosure provides methods for detecting the presence or absence of Sf9 rhabdovirus that is aggregated on and/or encapsidated in particles in a sample. In some embodiments, the sample is a protein, peptide, drug substance, biological product, vaccine antigen, or VLP preparation. In some embodiments, the method comprises the following steps: (i) subjecting the sample to treatment with an enzyme that will degrade RNA; (ii) subjecting the sample to one or more agents, such as a chaotropic agent, in order to stop enzymatic activity and disrupt particles; (iii) detecting the presence or absence of Sf9 rhabdovirus RNA in the resulting sample by RT-PCR. In further embodiments, the method comprises detecting the presence or absence of Sf9 rhabdovirus RNA in the sample by RT-PCR prior to subjecting the sample to the enzyme treatment in step (i). In some embodiments, the RNA signal detected after the steps (i) and (ii) is compared to the RNA signal detected prior to step (i). In some embodiments, RNA detected after enzyme treatment and disruption of particles is present in the sample in particles.

In one aspect, the present disclosure further provides fragments of the virus according to SEQ ID NO: 1, or fragments of the sequence that is complementary to SEQ ID NO: 1, wherein the fragments are labeled or chemically modified.

In one aspect, the present disclosure provides compositions comprising *S. exigua* cells and a rhabdovirus. In some embodiments, the rhabdovirus comprises a sequence having at least 70% homology to SEQ ID NO: 1. In some embodiments, the rhabdovirus comprises a sequence according to SEQ ID NO: 1.

DETAILED DESCRIPTION

Figure 1:
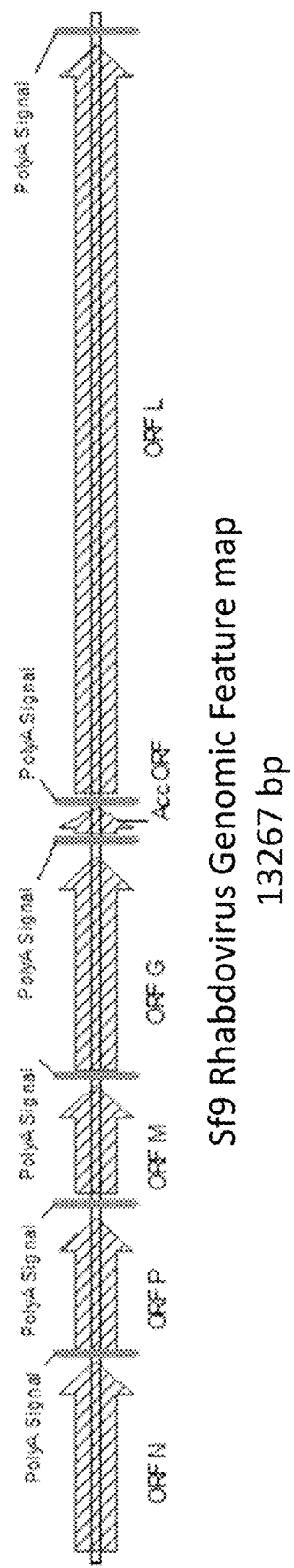
FIG. 1 provides a map of the Sf9 rhabdovirus genome, shown in the sense orientation (5' to 3').

The present disclosure provides compositions, methods, assays, and kits for identifying contaminating agents in a sample and/or for removing contaminating agents from a sample. In part, the disclosure provides a novel virus that was identified as present in the insect cell line Sf9 cells. Sf9 cells and other insect cell lines, which are commonly used in drug development to produce biological products for therapeutic purposes, have long been thought to be free of contaminating viruses. However, the present inventors surprisingly found that the novel virus disclosed herein was present in Sf9 cells. Based on the work described herein, the novel virus was determined to be a rhabdovirus. Although the rhabdovirus was found in cell lines other than Sf9, the rhabdovirus disclosed herein is herein termed "Sf9 rhabdovirus." The sequence of the Sf9 rhabdovirus is provided herein as SEQ ID NO: 1.

The present disclosure provides nucleic acids and other features of the virus, methods, assays, and kits for use in detecting the virus, and cells or biological products that are substantially free of the virus. In one embodiment, the biological products are products for therapeutic and/or diagnostic purposes. In a further embodiment, the biological products for therapeutic and/or diagnostic purposes are generated, at least in part, using an insect cell line. In a further embodiment, the insect cell line is Sf9 or Sf21.

In one aspect, the present disclosure provides compositions, assays, methods and kits for detecting the presence of a virus in Sf9 cells. In one aspect, the present disclosure provides compositions, assays, methods and kits for detecting the presence of a virus in a protein, peptide, drug substance, biological product, vaccine antigen, or VLP preparation. In a further embodiment, the drug substance was generated using, or produced in, insect cells such as Sf9 cells. In one aspect, the present disclosure provides compositions, assays, methods, and kits for determining if an Sf9 rhabdovirus is aggregated on or encapsulated within particles in a sample, such as a protein, peptide, drug substance, biological product, vaccine antigen, or VLP preparation. In one aspect, the present disclosure provides compositions, assays, methods, and kits for determining if an Sf9 rhabdovirus identified in a sample (e.g., a protein, peptide, drug substance, biological product, vaccine antigen, or VLP preparation) is capable of replication.

In one aspect, the present disclosure relates to the detection of a virus in a sample. In one embodiment, a target nucleic acid is isolated, amplified, and detected. Methods for isolating, amplifying, or detecting nucleic acids, including methods for detecting and amplifying target RNA sequences (for example, by reverse transcription PCR (RT-PCR)) are well known in the art, for example, in Sambrook et al, Molecular Cloning, A Laboratory Manual, Fourth Edition (2012) and Ausubel et al, Current Protocols in Molecular Biology (2011).

In one aspect, the present disclosure provides a method for detecting a virus comprising detecting a nucleic acid sequence comprising at least 25, at least 50, at least 100, at least 250, at least 500, at least 750, at least 1000, at least 1250, at last 1500, or at least 2000 contiguous nucleotides of SEQ ID NO: 1 or the reverse complement of SEQ ID NO: 1. In some embodiments, the method for detecting the virus disclosed herein comprises using one or more primers and one or more labeled probes in a PCR assay. In further embodiments, the method comprises using a forward primer having a sequence according to SEQ ID NO: 2 (TCTGTATTATGGGTTTGATCAGCTAAG) and a reverse primer having a sequence according to SEQ ID NO: 3 (CTCGCTGCTGAGCGGTTT). In some embodiments, the method comprises using a probe having a sequence according to SEQ ID NO: 4 (AGGATTGGAGAATTATAC).

In some embodiments, the present disclosure provides a virus according to SEQ ID NO: 1. In some embodiments, the present disclosure further provides fragments of the virus according to SEQ ID NO: 1, or fragments of the sequence that is complementary to SEQ ID NO: 1. In some embodiments, the fragments of the Sf9 rhabdovirus genome or the sequence complementary to the rhabdovirus genome are labeled or chemically modified.

In some embodiments, the present disclosure provides a labeled probe comprising a sequence that is capable of detecting the Sf9 rhabdovirus. In some embodiments, the labeled probe is complementary to a portion of the Sf9 rhabdovirus genome or to the reverse complement of a sequence in the Sf9 rhabdovirus genome.

In some embodiments, the sequence, fragment, or probe is labeled with a fluorophore selected from the group consisting of fluorescein and fluorescein derivatives such as, for example, FAM, VIC, JOE, 5-(2'-aminoethyl) aminonaphthalene-1-sulphonic acid, coumarin and coumarin derivatives, lucifer yellow, texas red, tetramethylrhodamine, 6-Carboxy Fluorescein, tetrachloro-6-carboxyfluorescein, 5-carboxyrhodamine and cyanine dyes. In one embodiment, the probe is labeled with 6-carboxy-fluorescein (FAM). In some embodiments, the present disclosure provides a method for detecting a virus wherein the method has a sensitivity level of between about 1 molecule of RNA and about 50 molecules of RNA. In further embodiments, the method has a sensitivity level of between about 2 molecules of RNA and about 20 molecules of RNA. In other embodiments, the sensitivity level of the method is about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 molecules of RNA.

In one aspect, the present disclosure provides a protein, peptide, drug substance, biological product, vaccine antigen, virus, or VLP preparation produced in an insect cell, or compositions comprising a protein, peptide, drug substance, biological product, vaccine antigen, virus, or VLP preparation produced in an insect cell. In some embodiments, the VLP preparation is a Calicivirus VLP preparation. In further embodiments, the VLP preparation is a Norovirus VLP preparation. VLP preparations include monovalent or multivalent VLP preparations that include one or more capsid proteins or portions of capsid proteins from one or more virus or viral strain. For example, Norovirus VLP preparations include monovalent or multivalent VLP preparations that include one or more capsid proteins or portions of capsid proteins from one or more Norovirus genogroups. "Monovalent VLPs" as used herein refer to VLPs that contain VLP antigens from a single viral strain, whereas "multivalent VLP" as used herein refers to VLPs that contain VLP antigens from two or more viral strains. Different Monovalent VLPs may be present together in the same VLP formulation. For example, in some embodiments, the Norovirus VLP preparations may comprise VP1 and/or VP2 capsid from one Norovirus genogroup, or may comprise VP1 and/or VP2 proteins from one Norovirus genogroup along with VP1 and/or VP2 proteins from a second Norovirus genogroup. An example of a Norovirus VLP preparation is the Norovirus genogroup I, genotype 1/Norovirus genogroup II, genotype 4 (GI.1/GII.4) bivalent VLP, which is described, for example, in U.S. Patent Application Publication No. 2013-0273102.

In one aspect, the present disclosure provides kits for detecting the presence or absence of a virus having a sequence of at least 50%, at least 55%, at least 60%, at least 65%, at least 70%, at least 75%, at least 80%, at least 85%, at least 90%, at least 95%, or at least 99% homology to SEQ ID NO: 1 in a sample, wherein the kit comprises one or more primers. In some embodiments, the kit comprises a forward primer, a reverse primer and a probe. In further embodiments, the forward primer has a sequence according to SEQ ID NO: 2; the reverse primer has a sequence according to SEQ ID NO: 3; and the probe has a sequence according to SEQ ID NO: 4. In some embodiments, the probe is labeled with a fluorophore selected from the group consisting of fluorescein and fluorescein derivatives such as, for example, FAM, VIC, JOE, 5-(2'-aminoethyl) aminonaphthalene-1-sulphonic acid, coumarin and coumarin derivatives, lucifer yellow, texas red, tetramethylrhodamine, 6-Carboxy Fluorescein, tetrachloro-6-carboxyfluoroscein, 5-carboxyrhodamine and cyanine dyes. In one embodiment, the probe is labeled with 6-carboxy-fluorescein (FAM).

In one aspect, the present disclosure provides compositions, methods, assays, and kits for a test to determine if Sf9 rhabdovirus is present in a sample, and to determine if the Sf9 rhabdovirus is capable of replication. In some embodiments, the method comprises detecting the presence or absence of Sf9 rhabdovirus in the sample by RT-PCR, wherein the method comprises using one or more primers and one or more labeled probes in a PCR assay, wherein the assay comprises the use of a forward primer having a sequence according to SEQ ID NO: 2 (TCTGTAT-TATGGGTTTGATCAGCTAAG) and a reverse primer having a sequence according to SEQ ID NO: 3 (CTCGCTGCT-GAGCGGTTT), and a labeled probe having a sequence according to SEQ ID NO: 4 (AGGATTGGAGAATTATAC). In embodiments, the present disclosure further provides methods for determining if the Sf9 rhabdovirus RNA signal in the sample is present in particles and/or aggregates, comprising subjecting the sample to RNase A treatment followed by treatment with a chaotropic agent in order to stop RNase A activity and disrupt particles. The treated sample is then subjected to RT-PCR assay as described above. An Sf9 rhabdovirus RNA signal in the resulting sample indicates that the Sf9 rhabdovirus is present in particles in the sample. In embodiments, the present disclosure further provides methods for determining if the Sf9 rhabdovirus RNA is capable of replication. To that end, the sample is incubated with a cell line permissive of SD rhabdovirus replication such as, for example, *S. exigua* cells, followed by passage of the cells. An increasing SD rhabdovirus RT-PCR signal indicates that the virus is capable of replication. Thus, the present disclosure provides kits for detecting the presence or absence of Sf9 rhabdovirus, as well as for assessing the infectivity of the Sf9 rhabdovirus. In embodiments, the kit comprises (i) forward and reverse primers and a probe for detection of Sf9 rhabdovirus RNA; (ii) an RNase; (iii) a chaotropic agent; and (iv) an *S. exigua* cell line.

In one aspect, the present disclosure provides insect cells that are free of rhabdovirus, rhabdovirus nucleic acids, or rhabdovirus particles, or free of rhabdovirus expression. In further embodiments, the insect cells are Sf9 or Sf21 cells. In some embodiments, the insect cells are free of the Sf9 rhabdovirus disclosed herein, free of Sf9 rhabdovirus nucleic acids or particle. In some embodiments, the rhabdovirus has been removed from the Sf9 or Sf21 cells. In other embodiments, the expression of rhabdovirus, rhabdovirus nucleic acids, or rhabdovirus particles is blocked in the insect cells. For example, in some embodiments, rhabdovirus expression is blocked by siRNA or antisense oligonucleotides targeted to the rhabdovirus genome. Thus, in some embodiments, the present disclosure provides fragments of the Sf9 rhabdovirus genome or the sequence complementary to the rhabdovirus genome. In further embodiments, the fragments of the Sf9 rhabdovirus genome or the sequence complementary to the rhabdovirus genome are labeled or chemically modified. Thus, in some embodiments, the present disclosure provides labeled or chemically modified siRNA or antisense oligonucleotides corresponding to SEQ ID NO: 1 or its complementary sequence.

In one aspect, the present disclosure provides methods for removing rhabdovirus from proteins, peptides, drug substances, biological products, vaccine antigens, or VLP preparations produced in insect cells. In some embodiments, the methods further comprise detecting the presence or absence of the rhabdovirus (e.g., Sf9 rhabdovirus) following purification. In some embodiments, the methods for removing rhabdovirus from proteins, peptides, drug substances, biological products, vaccine antigens, or VLP preparations produced in insect cells comprise, for example, chromatography (e.g., ion exchange chromatography, hydrophobic interaction chromatography, SDR HyperD chromatography, and other chromatographic methods known in the art and disclosed, for example, in U.S. Pat. No. 8,481,693, which is incorporated herein by reference in its entirety), filtration (e.g., ultrafiltration, diafiltration, and 0.2 µm filtration), treatment with detergent, or other purification methods, wherein the methods further comprise detecting the presence or absence of the rhabdovirus following purification.

Rhabdoviruses belong to the family Rhabdoviridiae (order: Mononegavirales) which is a diverse family of negative (−) sense RNA viruses that includes at least 6 genera: Lyssavirus (which includes, among others, rabies virus), vesiculovirus (which includes, among others, vesicular stomatitis virus (VSV)), ephemerovirus (which includes, among others, bovine ephemeral fever virus), cytorhabdovirus (which includes, among others, plant viruses such as lettuce necrotic yellows virus), nucleorhabdovirus (which includes, among others, plant viruses such as potato yellow dwarf virus), and norvirhabdovirus.

Insect cells such as cells from *Spodoptera frugiperda* and other Lepidopteran insect species are well known in the art and are commonly used to support the infection and replication of baculoviruses or other viruses for the production of recombinant proteins, for example, for production of therapeutic products including vaccines. The Sf9 cell line is a clonal isolate of Sf21 cells, originally obtained from *S. frugiperda* ovarian cells. Sf9 cell line ATCC CRL-1711 was deposited with the American Type Culture Collection (ATCC) in 1983. Other insect cell lines include, but are not limited to, *Spodoptera exigua, Heliothis virescens, Helicoverpa zea, Heliothis subflexa, Anticarsia gemmatalis*, and others.

The term "Sf9 rhabdovirus," as used herein, refers to the novel virus disclosed herein. The nucleic acid sequence of the Sf9 rhabdovirus is provided herein as SEQ ID NO: 1. As used herein, the term "replication competent" or "replication capable", when used to describe a Sf9 rhabdovirus or Sf9 rhabdovirus RNA molecule, means a virus or an RNA molecule which is self-replicating and provides for transcription in a host cell.

As used herein, the term "primer" refers to a series of nucleotide residues that has a sufficient number of bases to be used in a PCR reaction. A primer may be used to amplify, confirm, or reveal the presence of an identical, similar, or complementary DNA or RNA in a sample. As used herein, the term "probe" refers to a nucleic acid sequence used in the detection of identical, similar, or complementary nucleic acid sequences.

In one aspect, the present disclosure provides compositions, methods, assays, and kits for detecting a virus in a sample, or removing a virus from a sample, wherein the sample is a protein, peptide, drug substance, biological product, vaccine antigen, or VLP preparation. As used herein, the terms "virus-like particle and VLP" are used interchangeably and refer to a structure that in one attribute resembles a virus but which has not been demonstrated to be infectious. The term "drug substance, as used herein, refers to the material that contains a therapeutic drug and that is used to formulate, along with excipients, a pharmaceutical composition or drug product. A "biological product," as used herein, refers to a product or material that is produced by a cell or organism. The biological product may be a natural product of the organism, or may be produced by an organism that has been altered in some way such that it produces the biological product. Examples of biological products include, but are not limited to, vaccines, antibodies (e.g., monoclonal antibodies), therapeutic proteins, viruses (e.g., recombinant viruses for gene therapy such as, for example, a baculovirus), enzymes, growth factors, polysaccharides, nucleic acids including DNA and RNA, and particles (e.g., virus-like particles). Biological products may be altered, for example by glycosylation or radiolabeling.

In one aspect, the present disclosure provides compositions, methods, assays, and kits for detecting Sf9 rhabdovirus that is capable of replicating, or for determining if an Sf9 rhabdovirus is replication competent. Thus, in one aspect, the present disclosure provides means for determining if the Sf9 rhabdovirus present in a sample is capable of replication. In some embodiments, the method comprises incubating the sample comprising Sf9 rhabdovirus RNA signal with a cell line that is capable of supporting Sf9 rhabdovirus replication. In some embodiments, a cell line capable of supporting Sf9 rhabdovirus replication may be, for example, a *Spodoptera exigua* cell line. Several such cell lines are disclosed herein and include cell lines derived from *Spodoptera exigua* cells such as, for example, BCIRL/AMCY-SeE1, BCIRL/AMCY-SeE4, and BCIRL/AMCY-SeE5. In some embodiments, the *S. exigua* cell lines are cultured in EX-Cell 420 medium with 10% fetal bovine serum. In some embodiments, replicating Sf9 rhabdovirus is detected by measuring the SD rhabdovirus RNA signal by RT-PCR as disclosed herein at several time points. For example, in one embodiment, RT-PCR to detect Sf9 rhabdovirus RNA is conducted on samples prior to incubation with the cell line; immediately after incubation with the cell line (at passage 0), and after subsequent passages of the cell line (e.g., after passages 1 and 2). After at least one passage, an increase in the Sf9 rhabdovirus RNA signal as detected by RT-PCR indicates that the virus is replicating in the *S. exigua* cell line. A decrease in or lack of change in the Sf9 rhabdovirus RNA signal as detected by RT-PCR indicates that the SD rhabdovirus RNA signal is not associated with a virus that is capable of replication.

As used herein, the terminology that a cell line, sample, protein, peptide, drug substance, biological product, vaccine antigen, VLP preparation, and the like is "substantially free" of a virus means that the cell, sample, protein, peptide, drug substance, biological product, vaccine antigen, VLP preparation and the like does not comprise a detectable level of the virus as measured by a PCR or RT-PCR assay or the like.

In some embodiments, the compositions, methods, and kits described herein utilize enzymes to degrade RNA, such as ribonucleases (RNases). RNases are nucleases that degrade RNA. In some embodiments, RNases provide a thorough means to degrade a non-encapsidated RNA that might otherwise be resistant to degradation due to aggregation. RNases can be endoribonucleases such as RNase A, RNase H, RNase III, RNase I, and others; or exoribonucleases such as RNase II, RNase R, exoribonuclease I, or others. Ribonuclease A (RNase A) is a pancreatic ribonuclease often used in research, and specifically cleaves single-stranded RNA.

Chaotropic agents are known in the art and include, but are not limited to, butanol, ethanol, propanol, phenol, magnesium chloride, lithium perchlorate, lithium acetate, guanidinium chloride, sodium dodecyl sulfate, thiourea, and urea. Chaotropic agents weaken the hydrophobic effect of other molecules by disrupting hydrogen bonding. Thus, chaotropic agents disrupt the structure of and/or denature molecules such as nucleic acids, proteins, and lipid bilayers. In addition, chaotropic agents are capable of preventing the activity of RNase enzymes or DNase enzymes by denaturing the enzymes, and are also capable of disruption or disassembly of particles such as VLPs.

As used herein, the singular forms "a," "an," and "the" include plural terms unless the context of use clearly indicates otherwise. The term "or" is understood herein to be inclusive. The meaning of the phrase "at least one" is equivalent to the meaning of the phrase "one or more." The terms "comprise," "comprising," "containing," "having," and the like may mean "including" and the like. The use of the term "about" throughout this application is intended to indicate that a value includes the standard deviation of error for the method being employed to determine the value or, where appropriate, includes a value of 20% greater than or less than the recited value.

EXAMPLES

Example 1

Detection of Rhabdovirus in *Spodoptera frugiperda* Sf9 Insect Cell Line

End of production cell (EOPC) material resulting from recombinant baculovirus infection of the *Spodoptera frugiperda* Sf9 insect cell line was subjected to random screening for retroviral elements of insect origin. To this end, virus particle-associated RNA was prepared from EOPC material and was subjected to random primer RT-PCR cloning. DNA sequence analysis of resulting plasmid DNA clones allowed for the assembly of a sequence contig consistent with the presence of a replication competent rhabdovirus genome consisting of 13,267 nucleotides and containing six open reading frames. Homology searches at the amino acid sequence level revealed weak but consistent homology to the L protein of numerous rhabdoviruses with the highest homology scores associated with rhabdoviruses of plant origin.

qRT-PCR assays were developed for the Sf9 cell-associated rhabdovirus, and demonstrated consistent signals in total cellular RNA, conditioned medium, and baculovirus lysates of a working Sf9 cell bank. Similar signals were detected in the ATCC-derived Sf9 cell line (ATCC CRL-1711) which dates back to a 1983 freeze-down, indicating that the rhabdovirus contaminant was likely present in the original isolation of the Sf9 cell line.

Analysis of two human cell line samples harvested at different passage levels post exposure to EOPC material demonstrated a strong rhabdovirus signal in the passage 1 cells, but rapidly decreasing signals to background levels between passages 4 and 6 consistent with dilution of EOPC material with passage and demonstrating no apparent ability of the virus to replicate in human cells.

Norovirus VLP vaccines such as the Norwalk VLP and Consensus VLP vaccine formulations are described, for example, in U.S. Pat. Nos. 7,955,603, 8,431,116, 8,481,693, and 8,841,120; and U.S. Patent Application Publication Nos. 2011-0182975, 2013-0273102, and 2014-0004145, each of which is incorporated herein by reference in its entirety for all purposes. The intramuscular Norovirus GI.1/GII.4 Bivalent Virus-Like Particle (VLP) Vaccine Adjuvanted with Monophosphoryl Lipid A (MPL) and Aluminium Hydroxide ($Al(OH)_3$) has been tested in at least 133 subjects (a total of 234 subjects have been enrolled in studies; 133 subjects received vaccine and 101 received placebo).

Example 2

Random Primer Cloning and Analysis of Particle-Associated RNA Sequences in EOPC Material To detect possible RNA-containing virus or virus-like particles, we started with EOPC material for random RT-PCR cloning purposes. EOPC material was clarified of debris then subjected to nuclease digestion to eliminate free (not particle-associated) nucleic acids. Following nuclease digestion, the material was centrifuged at 100,000×g through a 20% sucrose cushion in order to collect virus particles. It was expected that significant amounts of intact baculovirus would also be collected in this process. High speed pelleted material was then subjected to nucleic acid extraction and then treated with RNase-free DNase in order to remove baculovirus and genomic DNA, while leaving any viral RNAs intact.

A random N9 primer tagged with a Not I restriction site at it 5' end (TATTGCGGCCGCTTCTTNNNNNNNNN) was used for both the first strand reverse transcriptase reaction and the second strand Klenow DNA polymerase reaction, resulting in double stranded DNAs that could be amplified using a PCR primer consisting of the Not I sequence tag (TATTGCGGCCGCTTCTT). PCR amplification resulted in the amplification of a few distinct bands indicating a limited amount of sequence complexity in the isolated RNA population. This procedure was repeated several times resulting in a different but distinct collection of bands each time (not unexpected due to the use of random priming). Of 142 clones that were initially sequenced, one clone was found to exhibit homology to an insect viral reverse transcriptase, while 32 clones were shown to be distantly homologous to the L protein of rhabdoviruses. The rhabdovirus homologies were observed at the amino acid sequence level only and were in the range of 24-26% homology through part of the L gene. The remaining sequences were found to represent ribosomal sequences, baculovirus sequences or sequences with no known homologies at the nucleotide or amino acid sequence levels. The isolation of baculovirus and ribosomal clones is an indication of the presence of certain RNA and DNA sequences that resisted nuclease treatment during the viral RNA isolation process.

Further sequence analysis of all of the clones showing rhabdovirus homology as well as the clones that showed no detectable homology to the Genbank database resulted in the building of two large sequence contigs of approximately 7,000 and 4,500 nucleotides, respectively, with each containing a portion of an open reading frame with homology to rhabdovirus L proteins. In order to determine if the two sequence contigs were part of the same viral genomic sequence, additional RT-PCR cloning was conducted using one primer from each contig. The additional cloning resulted in the isolation of clones representing the sequences spanning these two contigs. Finally, employing rapid amplification of cDNA ends (RACE) techniques allowed for the isolation of 5' and 3' end clones completing the sequence of the 13,267 nucleotide novel rhabdovirus genome (SEQ ID NO:1).

The feature map of the rhabdovirus genome is shown in FIG. 1. The map shows the sense orientation (5' to 3') of a negative strand RNA virus that is a member of the Rhabdoviridae family based on the following criteria:

1. Amino acid sequence homology between the large open reading frame of this virus and the L (large polymerase) genes of numerous rhabdovirus sequences reported in Genbank;
2. Genomic organization and sizes of the remaining genes is typical of rhabdoviruses in general;
3. The presence of a short accessory gene between G and L is common in many types of rhabdoviruses;
4. The absence of any homology between the N, P, M and G genes of this virus and any other virus. The latter is typical of rhabdoviruses which represent a large and very diverse group of viruses in which homology between members is often found only in the L gene product. (See Ammar et al., *Annu Rev Entomol* 54; 447 (2009); Jackson et al., *Annu. Rev. Phytopathol* 43, 623 (2005); Walker et al., *Virus Res.* 162(1-2), 110 (2011).)

The assignment of the N, P, M and G open reading frames was based on the standard rhabdovirus genomic layout and sizes of the coding sequences. Consistent with this was the fact that the G gene clearly encodes a type 1 membrane glycoprotein with expected hydrophobic signal peptide and transmembrane domains.

While the SD rhabdovirus was isolated from an insect cell line, homology relationships with other rhabdoviruses indicate that this may be a plant virus carried by an insect vector (see Table 1 below). Plant rhabdoviruses are often carried by insect vectors and generally replicate in the insect vectors multigenerationally (Ammar et al. (2009)). Indeed, the Sf9 cell line (a derivative of the original Sf21 cell line) was derived from ovarian tissue of *Spodoptera frugiperda* (fall armyworm) suggesting that the virus is capable of vertical transmission in the insect vector host (Vaughn et al., *In Vitro,* 13(4); 213 (1977)).

Examination of the homology data in Table 1 shows that the Sf9 rhabdovirus is distantly related to other rhabdoviruses via examination of L gene amino acid sequence homology. The hits with the highest scores are all plant rhabdoviruses followed by mammalian rhabdoviruses. Importantly, none of the other genes in the Sf9 rhabdovirus show any homology with any other virus at either the RNA or amino acid sequence level and this level of divergence is typical of plant rhabdoviruses (Ammar et al. (2009); Jackson et al. (2005); Walker et al. (2011)).

TABLE 1

Relatedness of the Sf9 rhabdovirus to other rhabdovirus L protein amino acid sequences.

Relatedness of Sf9 Cell Rhabdovirus to other published Rhabdovinis L protein amino acid sequences

| | Description | Max score | Total score | Query cover | E value | Max ident | Accession |
|---|---|---|---|---|---|---|---|
| 1 | L protein [Lettuce yellow mottle virus] >gb \|ABV56129.1\| | 399 | 399 | 53% | 2.00E−109 | 27% | YP_002308376.1 |
| 2 | RNA-dependent RNA polymerase [Lettuce necrotic yellows virus] | 339 | 399 | 54% | 3.00E−109 | 27% | YP_425092.1 |
| 3 | RNA-dependent RNA polymerase [Persimmon virus A] | 392 | 392 | 52% | 3.00E−107 | 27% | BAM36035.2 |
| 4 | polymerase [Barley yellow striate mosaic virus] | 380 | 380 | 63% | 1.00E−103 | 25% | ACT21686.1 |
| 5 | polymerase [Northern cereal mosaic virus] | 379 | 379 | 54% | 5.00E−103 | 27% | NP_597914.1 |
| 6 | polymerase protein [Northern cereal mosaic virus] | 379 | 379 | 54% | 5.00E−103 | 27% | ADE61677.1 |
| 7 | RNA-dependent RNA polymerase [Raspberry vein chlorosis virus] | 348 | 348 | 45% | 1.00E−96 | 27% | CBL76312.2 |
| 8 | L protein [Lettuce big-vein associated virus] >sp \|Q8B0U2.1\| | 345 | 345 | 50% | 8.00E−93 | 25% | YP_002308576.1 |
| 9 | L-protein [Lettuce big-vein associated virus] | 340 | 340 | 50% | 5.00E−91 | 25% | AFA36170.1 |
| 10 | polymerase [Sonchus yellow net virus] >sp \|P31332.1\| | 320 | 320 | 53% | 4.00E−85 | 25% | NP_042286.1 |
| 11 | L protein [Rice yellow stunt virus] | 311 | 311 | 49% | 3.00E−82 | 25% | BAI79332.1 |
| 12 | L [Maize mosaic virus] >sp \|Q6E0W6.1\| | 310 | 310 | 53% | 4.00E−82 | 25% | YP_052855.1 |
| 13 | putative RNA-dependent RNA polymerase [Strawberry crinkle virus] | 298 | 298 | 34% | 6.00E−82 | 29% | AAP03645.2 |
| 14 | large protein [Rice yellow stunt virus] >sp \|O10378.1\| | 303 | 303 | 51% | 8.00E−80 | 24% | NP_620502.1 |
| 15 | L protein [Australian bat lyssavirus] >sp \|Q9QSP0.2\| | 297 | 297 | 52% | 6.00E−78 | 25% | NP_478343.1 |
| 16 | polymerase [Bokeloh bat lyssavirus] | 297 | 297 | 54% | 7.00E−78 | 26% | AEL79469.1 |
| 17 | polymerase [Aravan virus] >gb \|ABV03822.1\| | 290 | 290 | 52% | 9.00E−76 | 25% | YP_007641396.1 |
| 18 | polymerase [Rabies virus] | 290 | 290 | 54% | 1.00E−75 | 25% | AFP66217.1 |
| 19 | polymerase [Rabies virus] | 290 | 290 | 54% | 1.00E−75 | 25% | AFP66212.1 |
| 20 | polymerase [Lagos bat virus] | 289 | 289 | 55% | 2.00E−75 | 25% | AFW16550.1 |
| 21 | polymerase [Rabies virus] | 289 | 289 | 54% | 2.00E−75 | 25% | ABZ81176.1 |
| 22 | polymerase [Irkut virus] >gb\|ABV03823.1\| | 289 | 289 | 52% | 2.00E−75 | 25% | YP_007641401.1 |
| 23 | large protein [Rabies virus] >gb\|ADZ98845.1\| | 289 | 289 | 54% | 2.00E−75 | 24% | ACR39383.1 |
| 24 | polymerase [Rabies virus] | 289 | 289 | 54% | 2.00E−75 | 25% | ABZ81226.1 |
| 25 | polymerase [Irkut virus] | 289 | 289 | 52% | 2.00E−75 | 25% | AFP74572.1 |
| 26 | polymerase [Khujand virus] | 288 | 332 | 68% | 3.00E−75 | 25% | ABV03824.1 |
| 27 | large protein [Rabies virus] | 288 | 288 | 54% | 3.00E−75 | 24% | ABU52978.1 |
| 28 | large protein [Rabies virus] | 288 | 288 | 54% | 4.00E−75 | 25% | ACF42345.1 |
| 29 | polymerase [Rabies virus] | 288 | 288 | 52% | 5.00E−75 | 25% | AFN24114.1 |
| 30 | large protein [Rabies virus] | 288 | 288 | 54% | 5.00E−75 | 24% | ADJ29912.1 |
| 31 | large protein [Rabies virus] | 287 | 287 | 54% | 6.00E−75 | 24% | AFM52659.1 |
| 32 | Large protein [Rabies virus] | 287 | 287 | 54% | 8.00E−75 | 25% | BAL45940.1 |
| 33 | large protein [Rabies virus] | 287 | 287 | 54% | 9.00E−75 | 24% | AFN27427.1 |
| 34 | polymerase protein [Lagos bat virus] | 287 | 287 | 52% | 1.00E−74 | 25% | ADD84516.1 |
| 35 | RNA-dependent RNA polymerase [Rabies virus] | 286 | 286 | 54% | 1.00E−74 | 24% | AEK98550.1 |
| 36 | large protein [Rabies virus] | 286 | 286 | 52% | 1.00E−74 | 25% | AFN27417.1 |
| 37 | polymerase protein [Shimoni bat virus] | 286 | 286 | 52% | 1.00E−74 | 25% | ADD84511.1 |
| 38 | L protein [Rabies virus] | 286 | 286 | 54% | 2.00E−74 | 25% | ADU55582.1 |
| 39 | L protein [Rabies virus] | 285 | 285 | 54% | 3.00E−74 | 24% | BAI43366.1 |
| 40 | RNA polymerase [Rabies virus] | 285 | 285 | 54% | 3.00E−74 | 25% | AEZ55976.1 |
| 41 | RNA dependent RNA polymerase [Rabies virus] | 285 | 285 | 54% | 3.00E−74 | 24% | BAM83861.1 |
| 42 | polymerase [Rabies virus] | 285 | 285 | 54% | 3.00E−74 | 25% | ABZ81201.1 |
| 43 | L protein [European bat lyssavirus 2] >sp\|A4UHQ7.1\| | 285 | 285 | 54% | 3.00E−74 | 25% | YP_001285397.1 |
| 44 | large protein [Rabies virus] | 285 | 285 | 54% | 3.00E−74 | 24% | AFP36387.1 |
| 45 | polymerase [Rabies virus] | 285 | 285 | 52% | 4.00E−74 | 25% | AFN24334.1 |
| 46 | RNA-dependent RNA polymerase [Rabies virus] | 285 | 285 | 54% | 5.00E−74 | 24% | ACP41226.1 |
| 47 | polymerase [Rabies virus] | 285 | 285 | 54% | 5.00E−74 | 24% | ABZ81196.1 |
| 48 | large protein [Rabies virus] | 284 | 284 | 54% | 5.00E−74 | 24% | AFN27407.1 |
| 49 | polymerase [European bat lyssavirus 2] | 284 | 284 | 54% | 5.00E−74 | 25% | ABZ81191.1 |
| 50 | RNA dependent RNA polymerase [Rabies virus] | 284 | 284 | 54% | 6.00E−74 | 24% | ADR03124.1 |

Example 3

Quantification of the Sf9 Rhabdovirus in Sf9 Cells, Conditioned Medium, and Baculovirus Lysates A Taqman qRT-PCR assay was developed in order to quantify Sf9 rhabdovirus RNA in various cultures fractions. The qRT-PCR assay used to quantify rhabdovirus RNA was a single step Taqman assay that employs forward and reverse primers in both the RT and PCR steps. Therefore the assay is capable of detecting both positive- and minus-strand RNA. The RNA standard employed in this assay as a positive control and for quantification purposes was a minus-strand RNA produced via in vitro transcription. Using this standard, the assay had a limit of detection of approximately 4 molecules of RNA.

The primer and probe sequences are located in a 64 nucleotide target sequence spanning nucleotide positions 7200-7264 within the L gene. The primer and probe sequences are as follows:

```
EOPC60 FWD: TCTGTATTATGGGTTTGATCAGCTAAG

EOPC60 REV: CTCGCTGCTGAGCGGTTT

EOPC60 Prb: 6FAM-AGGATTGGAGAATTATAC
```

A standard curve RNA for quantification purposes was prepared by in vitro transcription of EOPC clone 60 DNA using T7 RNA polymerase following linearization of the plasmid DNA. Template plasmid DNA was subsequently digested with DNase and the standard curve RNA was purified. An RNA of approximately 5 kb was expected but two RNAs of equal intensity, 3.5 kb and 5 kb, were produced as shown by gyoxal-agarose gel analysis. The smaller of the two RNAs is large enough to contain the target sequence and was likely produced as a result of premature transcription termination. For quantification purposes, the average molecular weight of the standard curve RNA is therefore 4.25 kb or $1.4 \times 10^6$ Daltons. The standard curve RNA was shown to yield only a trace signal when run in a PCR reaction without a reverse transcriptase step demonstrating that it was free of template DNA. Use of this RNA as a standard curve in the Taqman assay demonstrated a reproducible limit of detection of 0.01 fg of RNA which is equivalent to 4 molecules of standard curve RNA.

The EOPC 60 Taqman assay was used to follow the Sf9 rhabdovirus in Sf9 cell conditioned medium before and after membrane concentration and ultracentrifugation. These data are shown in Table 2 and demonstrate that the virus signal in the medium is not retained by 0.2 micron sterile filtration membrane but is fully retained by a 100,000 kD molecular weight cutoff membrane. In addition, $100,000 \times g$ centrifugation concentrates the virus signal into a pellet that can be resuspended into a smaller volume. These data are consistent with the presence of intact rhabdovirus particles in Sf9 cell conditioned medium.

TABLE 2

Sf9 rhabdovirus RNA signal in Sf9 cell-conditioned medium before and after membrane concentration and ultracentrifugation

| Sample | Description | Sterile Filtered? | Molecules/mL |
|---|---|---|---|
| 519.190 | Sf9 conditioned medium | N | 2.87e+07 |
| 490.194.1 | Sf9 conditioned medium | Y | 2.79e+07 |
| 490.194.2 | 100 kD retentate | N | 2.54e+08 |
| 490.194.3 | 100 kD retentate | Y | 4.01e+08 |
| 490.194.4 | 100 kD permeate | N | 0 |
| 490.194.5 | 100 kD permeate | Y | 0 |
| 490.194.6 | 100,000 × g supernatant of 490.194.2 | N | 1.84e+07 |
| 490.194.7 | 100,000 × g pellet resuspended in TBS | N | 3.48e+09 |

Table 3 shows additional data regarding the concentration of the Sf9 rhabdovirus in various sources of Sf9 conditioned medium, baculovirus lysates, and in total cellular RNA. Significant amounts of rhabdovirus RNA were detected in EOPC material (baculovirus lysates of Sf9 cells). Direct sampling of EOPC material demonstrated a rhabdovirus RNA concentration of approximately 2×10e+08 RNA copies per mL. When virus particles were collected from EOPC material by high speed centrifugation a titer of approximately 4.5×10e+07 was calculated. This four-fold discrepancy is consistent with the likelihood that direct sampling of EOPC material detects both particle-associated and free RNA while high speed centrifugation is specific for particle-associated RNAs. Rhabdovirus RNA signals were also detected in Sf9 cell conditioned medium at close to 10e+07 RNA copies per mL.

TABLE 3

Sf9 rhabdovirus concentrations in conditioned medium, baculovirus lysates, and total cellular RNA

| Sample | Description | PCR Sample size | PCR signal (fg) | RNA molecules/mL in original sample |
|---|---|---|---|---|
| 514.089DR | 100,000 × g pellet from baculovirus lysate | Equiv to 0.6 mL of original lysate | 53,980.86 | 3.87e+07 |
| 514.092DR | 100,000 × g pellet from baculovirus lysate | Equiv to 0.6 mL of original lysate | 68,867.60 | 5.02e+07 |
| 521.102B | Sf9/Baculovirus lysate | Equiv to 0.008 mL of lysate | 2581.37 | 1.39e+08 |
| 521.102B | Sf9/Baculovirus lysate | Equiv to 0.008 mL of lysate | 4183.10 | 2.25e+08 |

TABLE 3-continued

Sf9 rhabdovirus concentrations in conditioned medium, baculovirus lysates, and total cellular RNA

| Sample | Description | PCR Sample size | PCR signal (fg) | |
|---|---|---|---|---|
| 521.138 | Sf9/Baculovirus lysate | Equiv to 0.008 mL of lysate | 4688.83 | 2.52e+08 |
| 521.102A | Sf9 conditioned medium | Equiv to 0.008 mL of medium | 160.34 | 8.63e+06 |
| 521.102B | Sf9 conditioned medium | Equiv to 0.008 mL of medium | 181.64 | 9.78e+06 |
|  |  |  |  | RNA molecules/Cell |
| 521.160 | Sf9 cell total RNA Sf9 WCB | 4.4e+04 cells | 154652 | 1511 |
| 521.200 | Sf9 cell total RNA ATCC Sf9 cells (1983) | 4.4e+04 cells | 334567 | 3273 |

Regarding rhabdovirus RNA concentrations in viable Sf9 cells, log-phase Sf9 cells were found to contain approximately 1500 RNA copies per cell which is indicative of a low level infection and is consistent with the lack of observed cytopathicity. Data to support the notion that the rhabdovirus infection is inherent in the Sf9 cell line from its original isolation (Vaughn et al., 1977) and not due to a spurious contamination during routine culture come from analysis of the American Type Culture Collection (ATCC) Sf9 clone which was deposited in 1983 (ATCC CRL-1711). In this case the rhabdovirus RNA signal was detected at 3273 RNA copies per cell in the ATCC cell line, consistent with the levels seen within the Sf9 working cell bank (WCB).

Example 4

Sf9 Rhabdovirus Does Not Replicate in Human Cell Lines A549 and HEK293

HEK293 and A549 cells were tested for evidence of viral integration following treatment of these cells with EOPC material from Norwalk and Consensus VLP production runs. Norwalk VLP EOPC material (Meridian Part #85190, Lot 08110043) and Consensus VLP EOPC material (Meridian Part #85188, Lot 09110048) were tested for the presence of replication-competent retroviruses via culture on three human cell lines and were found to be negative due to the absence of amplifiable reverse transcriptase activity. Samples of these cell lines (Raji, 293, and A549 cells) at different passages post-inoculation were subjected to additional testing.

Additional frozen cell samples of A549 and HEK293 cells from passages 0, 1, 4, and 6 were tested for the presence of the Sf9 rhabdovirus RNA signal. To this end, cell samples were thawed and total cellular RNA was prepared and subjected to the EOPC60 qRT-PCR assay. These data are shown in Table 4 and demonstrate a strong rhabdovirus RNA signal in RNA of cells harvested at passage 0, but this signal falls off dramatically to background levels with continued passage of the cells in culture. These data are consistent with the dilution of the EOPC with passage and not with replication of the Sf9 isolated rhabdovirus. Therefore, there is no evidence that the Sf9 rhabdovirus is capable of replication in human cells.

TABLE 4

Evidence for the absence of Sf9 rhabdovirus replication in human cell lines A549 and HEK293

|  | A549 Cells - Exp527.044 Plate 1 | HEK293 Cells - Exp527.044 Plate 2 |
|---|---|---|
|  | fg rhabdovirus RNA/µL cellular RNA | |
| Consensus - P0 | 17209.00 | 12620.00 |
| Consensus - P1 | 381.44 | 17.33 |
| Consensus - P4 | 0.15 | 0.03 |
| Consensus - P6 | 0.06 | 0.01 |
| Norwalk - P0 | 41126.00 | 20141.00 |
| Norwalk - P1 | 994.42 | 21.81 |
| Norwalk - P4 | 0.15 | 0.06 |
| Norwalk - P6 | 0.02 | 0.00 |
| Not treated - P0 | 0.04 | 0.04 |
| Not treated - P1 | 0.03 | 0.02 |
| Not treated - P4 | 0.03 | 0.17 |
| Not treated - P6 | 0.03 | 0.08 |

Example 5

Testing of Norwalk Drug Substance for the Presence of Sf9 Rhabdovirus RNA

Norwalk VLP drug substance (NWDS13) was tested for the presence of a particle-associated rhabdovirus RNA signal by treating 4.5 mL of the drug substance sample with nucleases to eliminate any residual free nucleic acid then collecting particles via centrifugation at 100,000×g. Resuspended material was then dissolved with a chaotropic agent and RNA was purified. Prior to nuclease treatment and centrifugation, the sample was spiked with a sample of murine leukemia virus (MLV) as an internal control for recovery of enveloped virus particles. Subsequent MLV qRT-PCR analysis demonstrated good recovery of the MLV spike. RNA from this preparation was tested for the Sf9 rhabdovirus and a signal equivalent to 240 molecules of rhabdovirus RNA per mL in the original drug substance sample was detected. At a presumptive dose of 50 µg of each VLP we calculate that less than 10 molecules of rhabdovirus RNA per human dose. While the sample that was tested represents the particle-associated RNA present in drug substance it cannot be concluded that this is any indication of the presence of residual intact rhabdovirus particles with intact genomic RNA, especially since viral clearance studies have already demonstrated 15 to 18 logs of cumulative enveloped virus infectivity reduction using the norovirus VLP purification process.

Nuclease digestion was used in two different scenarios to eliminate free nucleic acids. In the case of EOPC material, nuclease digestion was used to eliminate free nucleic acids so that viral particle-associated RNA could be isolated for RT-PCR cloning. These are the experiments that led to the identification of the rhabdovirus cDNA clones. In these experiments, clarified EOPC material was titrated to pH 7.0 and Benzonase and Turbo DNase were added to a final concentration of 50 and 5 units/mL, respectively. Since EOPC material was based on Sf900II insect cell medium, the addition of magnesium was not required for activation of nuclease activity. Following nuclease addition, the material was incubated at 37° C. for 2 hours, after which EDTA was added to a final concentration of 20 mM. Viral particles were then collected by centrifugation at 100,000×g through a sucrose cushion and particle-associated nucleic acids were isolated using the QIAamp viral RNA isolation kit from Qiagen. This kit employs a chaotropic agent to inactivate any carried over nuclease activity resulting in the isolation of intact particle-associated RNA. This material was subsequently treated with the Turbo DNA-free kit from Life Technologies to eliminate baculovirus DNA that would have co-isolated with viral particle-associated RNA. While no internal controls were employed for the nuclease treatment steps, the fact that relatively few ribosomal or baculovirus sequences were identified in the resulting cDNA clones is indicative of the effectiveness of the nuclease treatment.

The second instance of the use of nucleases to eliminate free nucleic acids involved the testing of Norwalk VLP drug substance for the presence of particle-associated rhabdovirus sequences. In this case, the VLP sample was adjusted to pH 7.5 via the addition of Tris-HCl, pH 7.4, to a final concentration of 30 mM followed by titration with NaOH. After the addition of an internal control sample of murine leukemia virus (MLV), MgCl2 was then added to a final concentration of 10 mM and Benzonase and Turbo DNase were added to a final concentration of 25 and 5 units per mL, respectively. Nuclease digestion was allowed to proceed at 37 degrees C. for 1 hour, after which the sample was adjusted to 20 mM EDTA and was centrifuged at 100,000×g over a 20% sucrose cushion and RNA was isolated from the pellet using the MagMAX Viral RNA Isolation kit from Life Technologies. The internal MLV spike demonstrated that particle-associated RNA was protected from the nuclease digestion and was found in the final RNA preparation. While no controls were employed to monitor the extent of digestion of free nucleic acid, the use of significant quantities of nucleases in the presence of favorable reaction conditions would be expected to eliminate essentially all free nucleic acids, especially since only trace amounts of nucleic acid are present in drug substance.

The results of the studies indicated that a rhabdovirus of plant or insect origin has been identified in the Sf9 cell line and it is likely that this virus contamination is inherent in the Sf9 cell line from its original isolation. The Sf9 rhabdovirus genome was fully sequenced, demonstrating homology that is closest to plant rhabdoviruses, and it exhibits a genomic organization and open reading frame size distribution that is typical of all rhabdoviruses. Virus particles were detected in Sf9 cell conditioned medium and in baculovirus lysates and rhabdovirus RNA was quantified in terms of RNA copies per cell. There is no evidence of cytopathicity in Sf9 cells due to the endogenous infection. In addition, the studies indicated that the virus lacks the ability to replicate in human cells. The drug substance manufacturing process disclosed herein has been shown to effectively remove and/or inactivate enveloped viruses. For example, enveloped viruses may be disrupted by detergent treatment, and baculoviruses may be inactivated and removed by acid treatment followed by centrifugation to remove inactive and aggregated baculovirus. For example, steps in the process have been shown to remove model enveloped viruses, A-MuLV (cumulative>18.22 $\log_{10}$ reduction in the GI.1 DS manufacture and >15.73 $\log_{10}$ in the GII.4 DS manufacture) and AcNPV (cumulative>15.30 $\log_{10}$ reduction in the GI.1 DS manufacture and >11.54 $\log_{10}$ in the GII.4 DS manufacture).

Example 6

Analysis of Drug Substance for RNase A-Resistant Sf9 Rhabdovirus RNA Signals Example 5 describes the characterization of the novel rhabdovirus associated with Sf9 insect cells. One experiment reported evidence for a Benzonase-resistant, particle-associated Sf9 rhabdovirus RNA signal in one research lot of Norwalk VLP Drug Substance, indicating a possibility for the presence of small residual rhabdovirus RNA fragments either aggregated onto or packaged within Norovirus VLPs. In addition, the possibility for residual intact rhabdovirus particle contamination was not ruled out by the studies described in Example 5. Two lots each of purified Norwalk VLP drug substance material and Consensus VLP drug substance material were tested for Sf9 rhabdovirus RNA signals with and without prior RNase A treatment. The resulting data demonstrated that the Sf9 rhabdovirus RNA signals observed in drug substance were sensitive to RNase A degradation and did not represent RNA that is encapsidated in VLPs or residual Sf9 rhabdovirus particles. Appropriate steps were taken to control for RT-PCR inhibitors and to demonstrate that actual particle-associated rhabdovirus RNA is not susceptible to RNase A degradation.

In this study, experiments to further address the issue of a nuclease-resistant Sf9 rhabdovirus RNA signal in Norwalk and Consensus VLP drug substance were conducted by investigating a total of four lots of drug substance material and employing ribonuclease A (RNase A) as a more thorough means of degrading a non-encapsidated rhabdovirus RNA signal that might otherwise be resistant to degradation due to aggregation. After treatment of drug substance with and without RNase A, the experimental design included an RNA purification step in the presence of a chaotropic agent (to destroy RNase A activity) and quantification of any remaining Sf9 rhabdovirus RNA signal by a sensitive qRT-PCR assay.

Analysis of Norwalk Drug Substance. Norwalk drug substance material was incubated at pH 6.5 at 37° C. for 1 hour with or without the addition of RNase A to a final concentration of 10 μg/mL ($4\times10^{14}$ RNase A molecules/mL). Following incubation, samples were subjected to RNA purification using the MagMax viral isolation protocol which employs a strong chaotropic agent to immediately deactivate RNase activity and to disrupt any VLPs or viral particles that might be harboring encapsidated RNA. Purified RNA samples were further concentrated by speedvac drying and subjected to qRT-PCR analysis using an EOPC-60 qRTPCR assay described in Example 3. 840 μL of drug substance material was treated or not treated with RNase A and then subjected to RNA extraction under conditions denaturing for RNase activity. The final purified RNA samples were concentrated 84-fold from the original drug substance samples. 3×1 µL of each purified RNA sample was tested in triplicate qRT-PCR reactions.

Table 5 below shows the results of this experiment, in which only one of the two Norwalk VLP drug substance lots (NWDS 16) exhibited an Sf9 rhabdovirus RNA signal and this signal was equivalent to 51 RNA copies per mL in the original drug substance material. Norwalk drug substance lot NWDS09 failed to yield a signal (<12 RNA copies per mL in original drug substance). While lot NWDS 16 material was positive, the same material treated with RNase A exhibited no signal. This observation is consistent with the presence of the Sf9 rhabdovirus RNA signal in a non-particle-encapsidated (non-protected) state.

TABLE 5

Rhabdovirus RNA Ct values of Norwalk drug substance RNA samples with and without RNase A treatment prior to RNA extraction.

| Treatment | NWDS16 | NWDS09 |
| --- | --- | --- |
| None | 36.5* | ≥40 |
| RNase A | ≥40 | ≥40 |

*Ct value of 36.5 corresponds to 51 copies of Sf9 Rhabdovirus RNA per ML of original drug substance based on the PCR sample size and degree of sample concentration. Ct values of ≥40 indicate <12 RNA copies per mL in drug substance for sample sizes employed in this study and based on a limit of detection of 1 RNA copy per reaction.

Table 6 shows Ct values for the same samples following addition of a defined rhabdovirus RNA spike just prior to qRT-PCR analysis as a control for RT-PCR inhibitors. Similar Ct values for all four samples provided evidence for the absence of contaminating RT-PCR inhibitors.

TABLE 6

Rhabdovirus RNA Ct values for Norwalk drug substance samples spiked with control rhabdovirus RNA as a test for RT-PCR inhibitors.

| Treatment | NWDS16 | NWDS09 |
| --- | --- | --- |
| None | 20.36 | 20.73 |
| RNase A | 20.35 | 20.46 |

Analysis of Consensus drug substance material. Consensus drug substance material from R&D lot DCN12 or DCN15 was incubated at pH 6.5 at 37° C. for 1 hour with or without the addition of RNase A to a final concentration of 10 µg/mL ($4 \times 10^{14}$ RNase A molecules/mL). Following incubation, samples were subjected to RNA purification using the MagMax viral isolation protocol, which employs a strong chaotropic agent to immediately deactivate RNase activity and to disrupt any VLPs or viral particles that might be harboring encapsidated RNA. Purified RNA samples were further concentrated by speedvac drying and subjected to qRT-PCR analysis using the EOPC-60 qRT-PCR assay described in Example 3. 1000 µL of drug substance material was treated or not treated with RNase A and then subjected to RNA extraction under conditions denaturing for RNase activity. The final purified RNA samples were concentrated 100-fold from the original drug substance samples. 3×1 µL of each purified RNA sample was tested in triplicate qRT-PCR reactions.

Table 7 below shows the results of this experiment. Only one of the two Consensus VLP drug substance lots (DCN12) exhibited an Sf9 rhabdovirus RNA signal, and this signal was equivalent to 128 RNA copies per mL in the original drug substance material. Consensus drug substance lot DCN15 failed to yield a signal (<10 RNA copies per mL in original drug substance). While lot DCN12 material was positive, the same material treated with RNase A exhibited no signal. This observation was consistent with the presence of the Sf9 rhabdovirus RNA signal in a non-particle-encapsidated (non-protected) state.

TABLE 7

Rhabdovirus RNA Ct values of Consensus drug substance RNA samples with and without RNase A treatment prior to RNA extraction.

| Treatment | DCN12 | DCN15 |
| --- | --- | --- |
| None | 35.6* | ≥40 |
| RNase A | ≥40 | ≥40 |

*Ct value of 35.6 corresponds to 128 copies of Sf9 rhabdovirus RNA per mL of original drug substance based on the PCR sample size and degree of sample concentration. Ct values of ≥40 indicate <10 RNA copies per mL in drug substance for the sample size and degree of concentration employed in this experiment and based on a limit of detection of 1 RNA copy per reaction.

Table 8 shows Ct values for the same samples following addition of a defined rhabdovirus RNA spike just prior to qRT-PCR analysis as a control for RT-PCR inhibitors. Similar Ct values for all four samples provided evidence for the absence of contaminating RT-PCR inhibitors.

TABLE 8

Rhabdovirus RNA Ct values for consensus drug substance samples spiked with control rhabdovirus RNA as a test for RT-PCR inhibitors.

| Treatment | DCN12 | DCN15 |
| --- | --- | --- |
| None | 20.70 | 20.77 |
| RNase A | 20.81 | 20.69 |

Control Experiment to Demonstrate that RNase A Treatment Will Not Degrade RNA Inside Rhabdovirus Particles. Inasmuch as the above data provide evidence for the absence of encapsidated rhabdovirus RNA in purified Norwalk and Consensus VLP drug substance material, an additional control experiment was performed to demonstrate that RNase A treatment does not result in the reduction or elimination of RNA signals that are known to be encapsidated in viral particles. These data corroborate the data shown in Tables 6 and 8. In this control experiment, end of production (EOP) material, known to contain significant quantities of Sf9 rhabdovirus, was treated as described above for Norwalk and Consensus drug substance, and signals were quantified by RT-PCR. 280 µL of EOP material was treated or not treated with RNase A and then subjected to RNA extraction under conditions denaturing for RNase activity. The final purified RNA samples were concentrated 5.6-fold from the original EOP samples. 3×1 µL of each purified RNA sample was tested in triplicate qRT-PCR reactions. The data are provided in Table 9 below. RNase A treatment prior to the RNA extraction step had no effect on rhabdovirus RNA signals detected in EOP material. The stoichiometric ratio of RNase A to rhabdovirus RNA in EOP material was >10,000:1. These data demonstrate that a chaotropic agent can be successfully employed to inactivate a significant concentration of RNase A leading to successful purification of non-degraded, particle-associated RNA.

TABLE 9

Rhabdovirus RNA Ct values for EOP material with and without RNase A treatment prior to RNA extraction.

| Treatment | EOP Material |
| --- | --- |
| None | 14.57 |
| RNase A | 14.67 |

Example 7

Transmission Electron Microscopy (TEM) of Sf9 Rhabdovirus

The Sf9 rhabdovirus identified in Sf9 cell conditioned medium and baculovirus lysates was partially purified via tangential flow filtration and sucrose gradient centrifugation and was imaged by transmission electron microscopy (TEM). Numerous apparently enveloped, spherical to oblong particles were observed. Measurement of 270 particles revealed mean dimensions of 65.6×49.6 nm. These observations of viral particles are consistent with previous molecular biology data showing the presence of apparently functional, particle-associated, rhabdovirus genomic RNA in Sf9 cultures and lysates.

Figure 2:
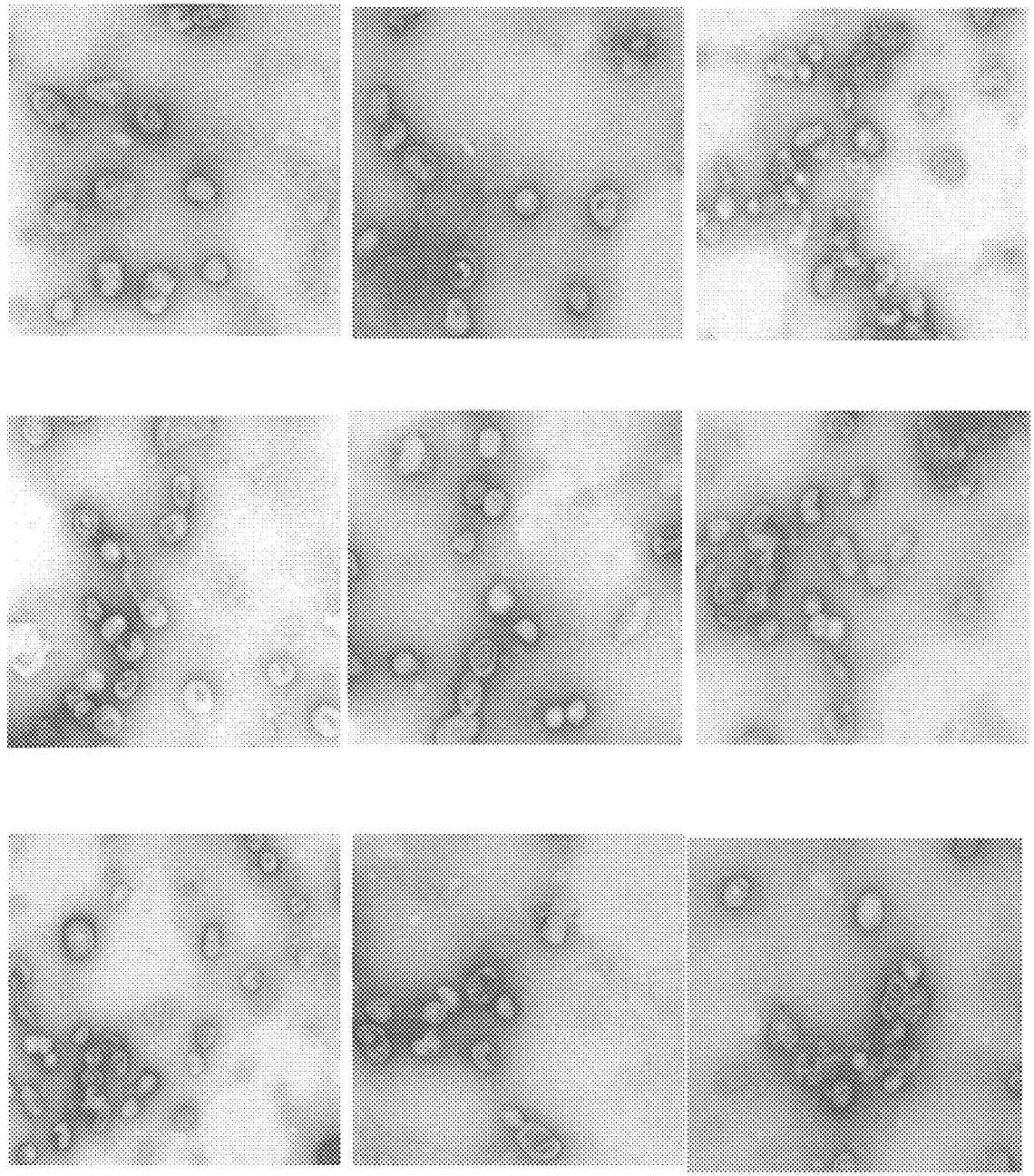
FIG. 2 provides 9 individual images of the Sf9 rhabdovirus, imaged by transmission electron microscopy (TEM).
Figure 3:
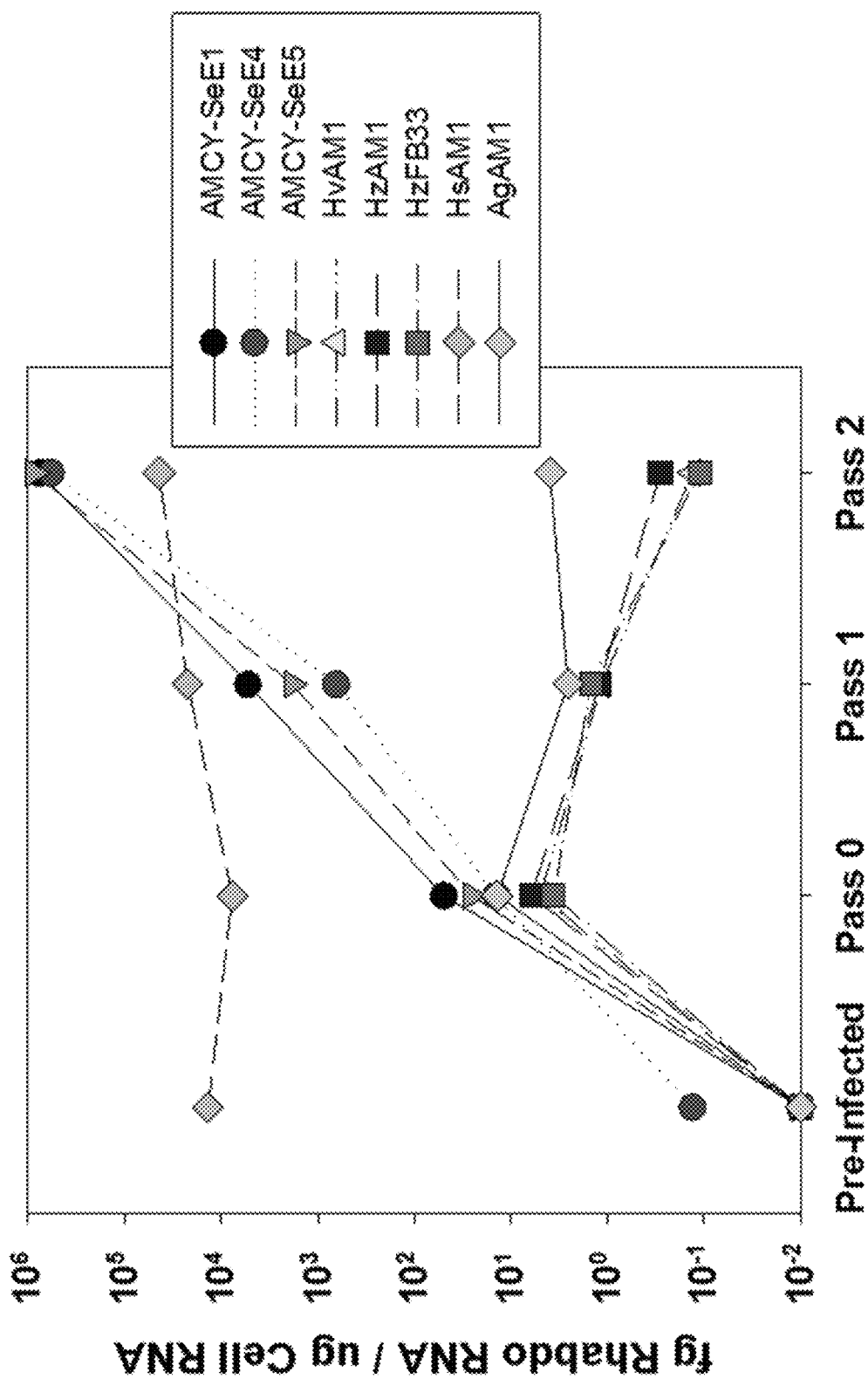
FIG. 3 is a graph showing the detection of Sf9 rhabdovirus RNA signals in insect cells (AMCY-SeE1, AMCY-SeE4, AMCY-SeE5, HvAM1, HzAM1, HzFB33, HsAM1, or AgAM1) exposed to Sf9 cell-conditioned medium at pre-infection or at passage 0, 1, or 2. Data are expressed as femtograms (fg) rhabdovirus RNA per µg of total cellular RNA.

In this study, experiments designed to generate transmission electron micrographs of the Sf9 rhabdovirus were conducted. A 10 liter wave bag culture of Sf9 cells infected with an "empty vector" baculovirus was established and was subsequently harvested. The clarified lysate was concentrated to approximately 112 mL by tangential flow filtration. Two times 6 mL of the concentrate was layered over two 20-60% sucrose density step gradients, respectively, and centrifuged at 100,000×g for 90 minutes at 10° C. The sucrose step solutions were prepared using a 10 mM citrate buffer, pH 6.0 containing 150 mMNaCl (citrate buffered saline, CBS). The sucrose gradients were fractionated into 1.5 mL fractions and fractions were analyzed using the Sf9 rhabdovirus-specific qRT-PCR assay (EOPC60 assay) described in Example 3. Peak fractions (fraction #13 from each gradient) containing the strongest Sf9 rhabdovirus signal were pooled. The pooled fractions were adjusted to a final volume of 32 mL with CBS, then layered over a 4 mL 30% sucrose cushion in CBS, and centrifuged at 100,000×g for 1 hour at 10° C. Following centrifugation, the supernatant was decanted and pelleted material was resuspended in 300 µL of CBS. This final material was subjected to TEM analysis following negative staining with uranyl acetate. Multiple micrographs were captured demonstrating the presence of numerous enveloped viral particles that were spherical to oblong and somewhat irregular in both size and shape. Most micrographs showed clean images with little in the way of debris or other material contaminating the purified viral particle preparation. Analysis of the dimensions of 270 particles demonstrated a mean size of 65.61±14.52× 49.56±11.58 nm. Representative TEM images are provided in FIG. 2.

Example 8

Insect Cell Infectivity Study

A study was conducted to demonstrate the ability of the rhabdovirus to replicate in additional select insect cell lines not previously infected with the virus.

The Sf9 rhabdovirus disclosed herein was initially discovered in Sf9 cell lysates following infection with recombinant baculoviruses, but the virus was also detected and quantified in Sf9 cell conditioned-medium independent of baculovirus infection. Rhabdovirus RNA levels within healthy Sf9 cells were quantified as well. The virus was identified in all Sf9 cells tested, and appeared to replicate at levels sufficiently low enough to not induce cytopathic effects.

To develop an infectivity assay for the Sf9 rhabdovirus, an experiment was initiated to determine if the Sf9 rhabdovirus could be propagated on additional insect cell lines. Table 10 shows a list of several insect cell lines received from the Agricultural Research Service (ARS) of the U.S. Department of Agriculture (USDA).

TABLE 10

List of cell lines received from the USDA for testing Sf9 rhabdovirus infectivity

| Cell Line Name | Species and Tissue of Origin |
| --- | --- |
| BCIRL/AMCY-SeE1 | *Spodoptera exigua* eggs |
| BCIRL/AMCY-SeE4 | *Spodoptera exigua* eggs |
| BCIRL/AMCY-SeE5 | *Spodoptera exigua* eggs |
| BCIRL/HvAM1 | *Heliothis virescens* ovaries |
| BCIRL/HzAM1 | *Helicoverpa zea* ovaries |
| BCIRL-HzFB33 | *Helicoverpa zea* fat bodies |
| BCIRL-HsAM1 | *Heliothis subflexa* ovaries |
| BCIRL-AgAM1 | *Anticarsia gemmatalis* ovaries |

Each of the cell lines provided in Table 10 was placed in a T25 tissue culture flask with 10 ml of EX-Cell 420 medium+10% fetal bovine serum, and was exposed to the Sf9 rhabdovirus by removing 5 mL of the culture medium and replacing it with 5 ml of conditioned medium from Sf9 cells that had been centrifuged and filtered through a 0.2 micron membrane in order to ensure no Sf9 cell carryover. The Sf9 conditioned medium was allowed to remain on the cell cultures for 24 hours, after which the medium was removed and the insect cell lines were further cultured in EX-Cell 420 medium+10% FBS. Upon reaching confluency, approximately 10% of the cells of each culture were collected and stored as a frozen cell pellet (p0) while new subcultures of each were established for continued growth and passaging. In this way two additional frozen cell pellets of each cell line were collected for passage numbers p1 and p2.

Following collection of the frozen cell samples from each cell line exposed to the Sf9 rhabdovirus, total cellular RNA was purified from each cell sample as well as from control cells from each cell line that were not exposed to the Sf9 rhabdovirus. Each RNA sample was tested in the Sf9 Rhabdovirus qRT-PCR assay described above for detection and quantification of any rhabdovirus RNA signals. Data were expressed in terms of "fg rhabdovirus RNA per µg of total cellular RNA" and are provided in FIG. 3.

Examination of the data in FIG. 3 leads to several significant observations. First, cell line HsAM1 exhibited an Sf9 rhabdovirus RNA signal prior to and following exposure to the Sf9 cell-conditioned medium, indicating that this cell line is already infected with the Sf9 rhabdovirus or a closely related relative. Further exposure to Sf9 cell-conditioned medium did not result in a further increase in the infectivity signal. Second, cell lines HvAM1, HzAM1, HzFB33, and AgAM1 did not exhibit the ability to significantly replicate the Sf9 rhabdovirus. Low level RNA signals were observed following immediate exposure to conditioned medium as would be expected, but these signals did no increase as would be expected in the case of virus replication in subsequent passages. Finally, and in contrast, the three *S. exigua* cell lines showed marked replication of the Sf9 rhabdovirus with RNA signals increasing by at least two orders of magnitude with each passage. The Sf9 rhabdovirus RNA signal levels in these cells at passage two are equivalent to those levels observed constitutively in Sf9 cells.

Thus, the results of the study showed that the Sf9 rhabdovirus (or a close relative) originally identified in the Sf9 *Spodoptera frugiperda* cell line is constitutively present in a second insect cell line from a different Lepidopteran species derived from *Heliothis* sublexa ovaries. In addition, the Sf9 rhabdovirus was observed to readily replicate in three *Spodoptera exigua* cell lines originally derived from *S. exigua* eggs.

Numerous modifications and variations in the invention as set forth in the above illustrative examples are expected to occur to those skilled in the art. Consequently only such limitations as appear in the appended claims should be placed on the invention. All publications cited herein are incorporated herein by reference in their entireties for all purposes.

REFERENCES

1. Ammar el D, Tsai C W, Whitfield A E, Redinbaugh M G, Hogenhout S A. Cellular and molecular aspects of rhabdovirus interactions with insect and plant hosts. Annu Rev Entomol, 54, 447-468 (2009).
2. Jackson A O, Dietzgen R G, Goodin M M, Bragg J N, Deng M. Biology of plant rhabdoviruses. Annu Rev Phytopathol, 43, 623-660 (2005).
3. Walker P J, Dietzgen R G, Joubert D A, Blasdell K R. Rhabdovirus accessory genes. Virus Res, 162(1-2), 110-125).
4. Vaughn J L, Goodwin R H, Tompkins G J, McCawley P. The establishment of two cell lines from the insect *Spodoptera frugiperda* (Lepidoptera; Noctuidae). In Vitro, 13(4), 213-217 (1977).

What is claimed is:

1. A rhabdovirus-free Sf9 or Sf21 insect cell comprising a biological product.

2. The insect cell of claim 1, wherein the insect cell is free of a nucleotide sequence having at least 70% homology to SEQ ID NO:1.

3. The insect cell of claim 1, wherein the insect cell is an Sf9 cell.

4. The insect cell of claim 3, wherein the Sf9 cell is derived from the cell line deposited as ATCC CRL-1711.

5. The insect cell of claim 1, wherein the biological product is a protein, peptide, drug substance, virus-like particle (VLP), DNA, RNA, virus, or vaccine antigen.

6. The insect cell of claim 1, wherein the biological product is a recombinant virus for gene therapy.

7. The insect cell of claim 1, wherein the biological product is a protein or virus-like particle (VLP).

8. The insect cell of claim 1, wherein the insect cell is free of a nucleotide sequence comprising the sequence according to SEQ ID NO: 1.

* * * * *

SEQUENCE LISTING

<160> NUMBER OF SEQ ID NOS: 4

<210> SEQ ID NO 1
<211> LENGTH: 13267
<212> TYPE: DNA
<213> ORGANISM: Rhabdovirus sp.

<400> SEQUENCE: 1
acataaaaaa atgaaaacaa tgaaacactg aactaattac atcctgaact gaactagaca 60
cacaaaatcc aatgaaaatt atacgataaa tgatcctaac tcttatagat gacaacgact 120
acttcacgga tatcggcttc ttagatctta tcatgacaca gggaaccatg aagccagtat 180
gggaagaatt ggggacagga gaaacagagt tccaagggac cgtggacatc ccagggagat 240
ctctcaagcc agaaaaaaca gattggagtg ttgatacatg tcgggagatc agtttaaatc 300
tgaagttacc tggtgaaata tggcaactgg cccatcaaga aaccatcttc aacagatttc 360
ttacatttta cgctactggg tatgttccaa atacacacac agccacagaa attgtactct 420
ccatggcatc actaatcttc aaggacaagg ccaaagcacc tattgatttg atttgggatg 480
actcatttca agctagtccc tctgatgagt gtgggttctc cgttgttgga gaaactccat 540
tggttatcgg acaacacccg gatgatgatg actacacatt gagagaagat gaagaatcag 600
ccgctatgaa tgaggaagaa aaaatacaag cagctctaaa aactttggga attcaagata 660
ctccagtaga cctgaaggat gcatctggaa ttgtctttga gacaaaggag gacagagaac 720
aaaggatcaa gaatgagaaa gctctacatg tagaggatga tatcaacgct ctaactcaga 780
ttacaaaaca attcttgttt gagtattcca caggctccct acagaaattt gttgcaaagg 840
ctactactat tttcatagat aataatgcta ctaacggctt cacccgtttg catctccatg 900
ccatcagagt catgaacttc attgctctaa caatgcttag aaaggtaacc aagtcaaatg 960
cccagatgat caatgccttt ctgaaggagc aatacaagag aaatattgcc tccctaatcc 1020
ccggcgccct ctcctctgag tttgctcctc ccagtaagag ctgcattgat aaactgacag 1080
ctatttctaa gaatgacccg gcagtcaatt cattctttgc aaaggttgtg atgctcaaca 1140
tggaggagga acggagaaac ccttctttgg ttgcttgtct tggggcttcc cttctcaccc 1200
acaccacttg gaatggaatg gggattttac atgttatttt tgaagtttgt ctattccatc 1260
agattagctg gaagaggttg gtcacagagt ccctgacctc actaacaaag atgtcatggg 1320
gtgaagtcag tcaattcctc atcaagtatc aagcaaaggg aaatcctgac ccaacggttg 1380
cctgggccag aatcattgat gattcttact ttatgagatt aaccacagta aatcatccca 1440
cacttgctgc attattagtg gaatccctca taagatctca gaaagatgat ggaatcctga 1500
atgccaactg ggccatccaa cacagggaca ccatcaatta ttatagggac gctgccaagc 1560

```
ttctcactga taagctcaca ggacagactg ctacagtcca agcccttacc aatgaagccg   1620
ctgatctagt tagaacaatg aatgcaggac cctctagata ccacccaagg cctagtaccc   1680
ttatccccat ggtagatcta aacccggaag acttataaga cttacctatt atcccaagac   1740
taatttccat aataatcccc aaaaagacaa ttactgttat tttctattaa aaaaccaatg   1800
aaaattatgc agagaatatt gagacatata gtatccttct tctcaaagtc ctggtgccaa   1860
tcctccgatc ccgctctagt gtgcgactgt gagtatcctc ctctcaagag aaactatcaa   1920
ctgatttact ctataatggc ttcccactct cttgacacca ttgatctatc tgaaattgga   1980
ttgacaaggg aggttctgac tggggttggc gattacatga ctggacaaag accggttcca   2040
gccttcaatc ctccagaggt cggtcactcc ccctctgatg aagtggcaaa acgattggga   2100
gaactgaaga attactggac tcagttagag gatcctcttg atgagagaat tctcaatacc   2160
ttgaaagcga tcagcatcct gagcggagac accagaggag atctgagtgg aaaatataaa   2220
catctagtcc gcattagcgg agatgacatg ccccaattat tggacgaact tatagacatc   2280
tgtcttctgg ggcctaagac tctaattgct accttacgaa tggcgataac cgcctatacc   2340
gctgcattag ccagaaatgc caagtccacc atctcagata ttactaccgc atcagcagat   2400
ttgatggtca tcactcagat gatacagtcc cagcaggaat cttttccaatc atcattagag   2460 catctctctc atgcttggaa taacgtcgcc agtggtatga ctgcttatac agcggaactg   2520
gataagagaa ccctcaagtt gacacagctt acaccgccag tcaagcctga ccatcaccgg   2580
gccccctcta cagcctccag tcatacccct gatgcttcag tggggcttca tataaacata   2640 accccggtt gtgcatataa gtcccaattt ggggtattga cttgctgtcc caatgggaac   2700
attggttttc ttgcaaataa ctccgatggc actgtgatag ccaaacttgt ggaagtaatt   2760
aggaagccac gccctctcac gacggccctc aataagaacc tgtctgagct gatcaattat   2820
gtcaaggcaa atccgaagat ccttgctact tactctacct cttctcctca ggataagctt   2880
aatatcctga atgagatcca cttctgcatc ccagatctta ccaatcaatg ggtcaaggcc   2940
tgataacatt cccttccctc acaaactcta aagatatctc catccttgat gacattttta   3000
ttaattatat ttaagtacga tttaagatct acataccaaa accaaccatt ttgatgatta   3060
acatgttatt ataaaaaacc aatgaaaactt atacgttaat tgagataagt ttgatttcat   3120
tgttccttgt gtcatcaccg aacttttttga gctcgaacaa tgagtgctct tgaacggatt   3180
gcacggagcc tatcattgaa gaagttgaac cctaggagaa ctccaaagac tcagcctatt   3240
cctgaaaagg ctactgtcta tcatcctttc atgctctctt atgatctcaa tttagctatt   3300
gagggtaaaa tccacatctc cgctatcacc attatagtga atgcccttc cttagcttgg   3360 gcaatagaac tctttcactc tgactcatcg tggtcagggt gtcttgagta cttttggaaa   3420
tccatcaagg ataacatatt ggcatccata aaccctcgag ttgatccaaa tggaacatgt   3480
catatgatga catcaatcat aactttcctc ggattctcag atggatcctg catcaactca   3540
gaagcagagc caagacagct cacaggatct agatcctggg agatcatgtc tcctaatcag   3600
aatctcattg tgataaccct aggattcaaa ataaccttga aaccttcgc acagcaccag   3660 agatacagct tgcgtgacca tggattccac aaattggaga tgctcaacga gaaagagaag   3720
aaaatgttga actatatggg ggtcaaacaa ttaaaacccc agtatacaca tgaaaagaca   3780
ttcgagaaac tcattctcaa gaacaaaggt ccaaagggt ctcgtgtcag ggcaattctt   3840
cactctcaaa gtcgtgacat gtggtctcca accgctcctt ctcctccacc cacatatgaa   3900
```

```
gatggatcct cagatgaatg ggatcagcaa caactgcaca gcctcaacca cctgcataca    3960
ccttctgtcc ccctgagggc ccccaggaca tccccacccc aacaactctc ccaaaaccg    4020 acatccacaa cccaacccct cccacaactc acacaaccaa acaagcccca agaactctcc    4080
aagtagacac ttgacagccc ccaccaatta cttttagatc ataaaaaacc aacaggcaga    4140
atataagacc tatcaattag agatattaaa aaatactaat taaacaatta tacatcaagc    4200
attggctcat tatggttttc ttaagtttat caacgatcat atttatccta agcctccggg    4260
ctgtaacctg ctccaatcct ctctcctatc ctaatggcat tttgactaac aactctactc    4320
acaatcatcc cctatcggac ttttatattt tttatgagaa cagttccctt acctatactc    4380
aattccctgt ggccccagac tgctctagta ttctagatac tagagatgag cagtatccca    4440
ccactgttac tttgtggaag gttgatcaag aatctcaagc tgagtgggga ctccttttat    4500
ggcaagagag aattgacacc acttgctcct ggaacttctg gggcaattac aaaggatcca    4560
ttgtatctaa atcctcagta cctctaaagg atatcccatc gggtagtgcc cggaatggat    4620
attgggcttt gagcaatgat gaagttcaag agattgatca tgtcccttac aacttgagat    4680
attattgtta ctggtgcaga aatgaatatc ctgggagctt ttatatgaga tatgtaaaga    4740
aagttcggat cataagaaat cctgatgggt ctataaagac tcctagagga tcctgggttc    4800
atgagttgga caacttgtgg ggagatcaga tgaggtatct agttattcga agatttgggg    4860
gagaatctag ctgccctctt aagatatatg atgtgagagc aggggttctg tcaaaatctc    4920
ggtcaaactt catcttagtg tcccttccct ccttgaattt gcagttctct gtatcacttg    4980
aatccactga gacgaaatgc tcatttggag ataagacata tgatattgtg cagagcatgg    5040
gaggctatct cctctccatc gacataggta atgcgaactg gcgaggccct gggatccta    5100 cccctcagca tccgggtcgt gaaagaagat caattatgga gtttccggat caaacatctt    5160
tcagatataa ccaatttata aattatcact catccccaag acacaagaga catgatcaag    5220
aatttgagtt ccctctcagt ctaaaatcca gttatgatta tgctcaattt agatatgagc    5280
agaatttcat catccgacag atcaataaga attttggatt attacagaag agcatttgtg    5340
atattcagtt ttctaagtgg cagaatctca gtccacccaa tcttgctatg aaaattgctc    5400
attatgtcac cggctctatc cactctatag gtggtgttca tcatggatct tattcaattc    5460
aaagaacgga aaaatccatt actaaggtca atctggtgtt tcccattgtt attgttcatg    5520
gaatgtataa gtgccaaagg gaaccatcca aggaggtggt ttgggcagaa cccgtcacag    5580
ggatcttatt caagtctcct attccgactc atttctcact aagttcctct tggctacctg    5640
gggtaaatgg ttcttctatt gtccctctga caggtcaaat tcttctccct gaaatcacaa    5700
tggatcactt ggaggttgta caacaggttg aagcaaagat ggtcaaaagt atgtacacga    5760
atgtagagtt gtttggatca acagaggaat ttcaaagata ccaaactcag ggaattacct    5820
ctgatgaaca atcaaataca gtaaatcctt ggattgggct tttgatacat ggtgagtgt    5880 ccatagctac tggaatatta gtagcacttt tgatcccctc aatcttaaaa ttgttcagac    5940
atataattga gaaggggag gcatcgttag aggagaggtt gcatctgagg gaaacctcaa    6000
gaaaagaatt tgtcaaggtt aggggaaac catgggtgt ctaagctacc acagcttcca    6060
caagagattg gactccaggt ggctctctcc atcaagcgat catgactcac aaagtcccctt    6120 caggccctaa cagatcagta cagccatcat tcatttgggc tccatctggc cccaaccgac    6180
tcctcttata aaaaccaat gaaacttata cagatcgtcc ttgactgcca aaatggatct    6240
cactttagac actatgaggc atattgaaac tctgatcaat tcacatctag agcttgaaga    6300
```

```
ccttaaatct tgattacag acacttgttt gattcactca agggatctat acaatccctt    6360
cttatacatt atctgttttg tcaaacctac catcacagcc agtgctgaaa actttatgat    6420
tgggaaatta agaagatca tattccttct tctattttc ggttaagtca ccaaactacc     6480
tatcaaacca atacatgaga acagtgtatt attcctgcta ttaaaaaaga tcataccttt    6540
tccatctcag ctcctcagtc aaatcttagt ttcattaaat caccatggac gaattacaaa   6600
gtgataatgt ccgtaaaaaa cgtccccctt tatcaactca ttgtgacacc cctctcaccc   6660
tcaacaatgc cagaaaagcc ttattagtac ctgcacccgg tcaattcata catcccaata   6720
accccattcg acgagagtac ttggagatgc agagacaact tcagataaca cccccccaatc  6780
tatttgatct atcaaaagtt cagggttttt cctaaatgt gtttaatgta ccagtctcta    6840
gccttccttt attagaattt agacaagcat tgcacttggc ttctcaacta taccaagtag   6900
aagttgaagg ggttctcaaa gagctagggg catcagctac taaaattgat atatctcctc   6960
tgatgaaaaa taaggactta attaatcttt atctgagaaa atgtttctgg gaggaagcag   7020
ttgtcatgag tggaaatgat aactctagtc agggatcctg gtggtcaaga gcagataaag   7080
agcttattct ctttagacga cctgggcttg atatcataat tggggagaat ttaatgtcaa   7140
tccagacatc tcagaactcc atattggtct cccgagatca tctaaccata ttgtcagatc   7200
tcgctgctga gcggtttagt ataattctcc aatccttctt agctgatcaa acccataata   7260
cagatatgcc caccccttcc gaattaagtt tatttcttaa ggaaggagat gaaatgctaa   7320
ctttagcagg aaatcaagga tatgatctaa tttatacttt agaatcttcc tgtacttccc   7380
gattagtagg gaactatgaa ggaggctcgt ggaaagattc taaattccgg catgaaattg   7440
ttaaagattt agagaaaaga gcctcagatc taaatttaca tcctcaactt agagttagag   7500
aacaactgtt agattcagtt tttgaacgaa atctaaacgc cttcacccaa ctgtatgggc   7560
tatatcgcat atggggtcac ccaactctgt atccattact tgggacaata gccctcaaag   7620
aattgggaac aacaccaaga ttgtacctat cacaccaagc tcaggagatt aacaacaagt   7680
ttaaggaaga gttcataaaa agatatttaa atagacataa ggagtggccg gaattagatg   7740
tatcgaaatt accaagacat aacatcattc gagtccatta tgagaagaaa ttacaatttc   7800
cttctaaatc cagacaatat aggagatctc atctctcctt ggtagaattc aaagatgtat   7860
tccctgttga tcctaaattt gatcttattg aatttattga tgataaatcc atctccttag   7920
gtttcccaga tctccttaac gagatctata gaaacaagag tatcgggaat tcactagcaa   7980
gatccttatt gcttaatttc ctctcctctg acatttcaga cccccaagaa tttctgaaga   8040
atatagatac ctcagggttt cctcctgaag agatttgtgt tggggtacac gaaaaagaga   8100
gagaaggaaa gctaaaggca aggctgtttg gattactgac cttagtgaaa cgatcatatg   8160
tagttatcac agaaaaactc ttggctgagc atctatttcc gtatttccct gaaataacca   8220
tgacggatga cgagtagtt ttggagaaaa agaggcatgc attcaataca gaacgaaaaa    8280
acaaatttat ggtgagtttg gattttttcca agtggaacac caatatgaga gccccagaca   8340
cacagccatt ttaccacact atagatacga tgtttggttt ggaaaattgt tttaccagga   8400
cacatgaaat gttctacaat tccttttgt accttataga cggttcttat ctcccaacaa    8460
tagttgatga tgggttcaaa acagatattg gatgttggcg acatcatctt gggggaatcg   8520
aaggtctcag acaaaaagga tggactctgt ggacagttat gttgatcagg ctagttgcgg   8580
aaaaatatat tttcaatatg tctatcatgg gacaggggga caatcaaatg ctacttctaa   8640
```

-continued

```
ctttcgattc taatacccg gaagaatatg ccctctctca agttaatgat ttccttcagt    8700
cattaaagga taaactgtca ctaataggtc ctcctctcaa gttggaggaa acttggattt    8760
ccaaagactt ttatttatat ggaaagtatc ctatcaaagg aggtgtttct ctcaccacat    8820
cgtggaaaaa atcatgcaga atgttccgat gttgcaacga ggactatccc accatagagt    8880
ccagtttgtc ctccttagct gcaaacctgt actctgcagt ggctgctgat aactttacac    8940
agactctgtt ttttgtttac ttatttgaat tagtaggtct attccaatgc aatattagaa    9000
gaccctatct ccaaaagaac tcattttatc aatcgttaga tcgaaataga accttcacag    9060
ttgcttctgc aaaagaccaa agaagaaac ttcatgtccc tcttgttcta tcacccccaa     9120
atcagctaca gcctaccgag gttttgttag gactatgttt gactccgagg actttgggag    9180
gatatccagt tgttctgtac ccatcggtct tgataaaggg agcccagac caattatcat      9240
ttgatcttgc gtccttaaaa ttattttcaa agtcagcaga tgcaactgtt aataggataa     9300
taacccgtgt atccagtcca ttcctctccg agtataagaa ttattttcta cttttttatga    9360
accctgaggc aattaacctg gagtctacac ccactcctgc agaggcaagg agaactacga     9420
tgttagaatt tctttccaac agtgatcgtg ttaaccagcc ttacataaaa gaattcctaa     9480
acatcattca tgagaatgca aatcaatcta tggaagattt tttaacctca aatcctgtac    9540
ttcatccacg tgtaatctct cttctatttc aggcaactcc acaatacaga gctcaacaag    9600
taattggaag gctccaaaag accccaacaa tggctagagt ctacttaaga gagggagata    9660
gagatcttta tgcactgtta gagatgtctg agttgaatca ttttaagtca gtattcgac     9720
aagtctttgc tgaggtaggc aggtattcat tgcctcactt caactctttg gttgaacatt    9780
ccacctttt aaggaacatg ggttggggta aaataattga aggtgtagat agtgcccctc      9840
ctcatgaggt cttccatcta gaggtcatga catctattac agaatgccag gattctccac    9900
atgcagacct ggggttcata tcagttagac tgaacacccc taaagatgtt gcaggaaatt    9960
ctcttgcaat tggaaccaca agaccttata gaggatctat cactaaaaat aaagtcaact    10020
ccttatcaac aaaaatccaa gccagaaccc cttctctgtt acaaagagct ctcatggttg    10080
caggactgga atcctgggca ttcactaagg attcttcact tgctcagtta tcaagggggt    10140
tagtttggag tgttacagac ttaccgtatg aactgttgac tccacaggta gatcaggttt     10200
cgggatcata tcaacatcac ttcgaaatg atagactaga caatgggga atcagtcctg       10260
ttttaccgaa tcaaggtacc aaattacaat tcaacactgt ccctcttgta tgtttgaata    10320
aaggaagtaa aaataagaat gtcatgttcc aagggccttt agtgatgttt ggaagtgtaa    10380
ttggcgaggg actgcttaca gaaggtatca attatccaga gacaaaacta tttcacatcc    10440
atattaggaa tccctcttcc atacaggatc ttgatgaaaa tccaatcacc tatccccta    10500
ttcaacagcc tatcagattg ttacgaaacc cccaatctcc tttcttatt ttcccatctg    10560
acaaaatcat gccttatata aaagaattc taaaatatcc tatctgttca cgggaagatc    10620
tcaatgtgat ttctacagaa tctcgcttca atactttatt ggcctacgag tgcataaact    10680
tgcttgatcc atggtcatgg gtctctggat ctgactcgag attggtaact aacggaataa    10740
ccatcaactg gctctctct tgtaatattg tagagctatg tcttgtgatc agcctcttac    10800
ttctagctat tttcttcacc ccaactaaaa tcattgatcc ggaatggcat atcaatagag    10860
tgataaatgt tgtcaaagct tcccctctct cctcatggga gaatttaaca aatctctgtt    10920
tctgcaatgt cttcccaacc cctctattac atttcttag agctatgagc ccacaaactt    10980
ctgagggttt aacaaattca aatgttgcac ttatactaaa gacttccatt acattgatcc    11040
```

```
ttcagaatat ccttcacgat aggaatttca taaaaggaaa agtacctcac ctgattgcac    11100 cccccggctgt gtcttttaac ctgcacccct acagggtcat agaaatccta gggtggttat    11160
ataaggaaca tgaagttcat aaatcccatc tttcatacct ctctaaggac atgctagatt    11220
tgaaacttag gagtttggaa ggtccctatg ttcaccaatt agactttttgg gggagcccta    11280 cccgaatatc tggaatcagc tctgagtctc tggattatct ttgtaaattg gaagacgtaa    11340
ttaaatctag atccatagag gtactcacag ttgctacaat atttgatcca aatccactcc    11400
caatgcctct agttactggc cccattgtta agtcgggtgt tgtgaacaca aggctgcaag    11460
tatcttttta ttcagagggg gacgtactgc atccggaatt aggacataga gattatagaa    11520 cttcttttt ccgaccagct ccattgccca catcaggggc ttataagcta tcaagtgttt    11580
tgcccttact aggaagctgt gccttgacaa aatgcctctg tttagctgat ggaacaggtg    11640
gattcaccag aacactcgct cttagagatg attcgaaaac aattgtattc aatacattag    11700
taactgatca agattatgta acacaaatgg acccaattca aaatatccca gacattgcag    11760
atcttccaat ttcttgtcag aagaaagttg tgggcctaag ggaggtcaat gattatccaa    11820
cagatataac aagcccggat ttcggacatc aaattctgga cagatttgga ggtgatttca    11880
tcttggttac aggagatgcg gaagacccct ctctgcacca tagtgggaat gttttagctt    11940
tgttcaaagc ctatatggat attagcctaa ttgtgaattc cgttcatggt atctttaaga    12000
ttcatactca cagaaggtct gtcctacatc aggctctggt tatattgttg acttattatg    12060
actctgtagt tgtagtaaga agtcaattct ctctccgatc caacaatgaa ttttatcttg    12120
ttggtgcaag aaacaagtta gctcctaaaa tccttccact aaatattatt actctggcag    12180
atggtaatcc gaccctaaat gttggtctaa gcagagatgc tgaactgatg ctgaataaaa    12240
gtctcaacaa cttaaataga caacaaggtc aactgcaaga gctacaaaaa tctacctaca    12300
tacagattac atccaactta atgcctcacc tccattacca agatctaatc tttcacctag    12360
ttggtcagta tccatggttg aaacaggaat actttgatat cggggaatcc aaggatgggg    12420
atctcagacc tatctactca tcttgtatcc ataagtttgt aacctctata cacaaggcaa    12480
ataccaaata tgaggagaaa gatgtagcaa gatttgtggt aaagcaattt actctaagag    12540
agctgtcaga tatattatcc tcctatctct ttctgatact gtctgttctt cccctagcca    12600
gatggaattc ttggatacct cacttcttga agaaggatg cttgttatgg atacaatgtg    12660
agaatgggtt gtggttcttt tctccctatc tgggggttgt cccacctgcg agatcaacct    12720
atcattttag actgtatagg acacaagatt tattaaatca tgttgcgatc cagaggattt    12780
gcagatctgt tggtttagct cacatgttac acttcaggga acctgacgat aaacatctta    12840
aagaagagtt catctttact agaccatcaa ggaaattcac attctatgat cctaaactca    12900
agggactaaa agacaagatt aaatgtcaga gttggcaatg gctcagtcaa tctcctggtt    12960
atcaactgga tcagtttgct cgaatttccc aaaatcccaa gaaataagga gcatctatca    13020
aatcacccga ccaatgattg tctctttgtc ctccatcaaa ctatatataa atcaatcaat    13080
cgtcttaaag ttctcttgat ttttgttgta tagattataa aaaaccaatt attttaatta    13140
cttctctcat ttacagttag tgtcccttaa gaatatctgg cttcatgtca tcaagggtgg    13200
accctctatt ttatcttcat tttctctcag caacccactg catcaatcat ttcttcccct    13260
gcttgcc                                                              13267
```

<210> SEQ ID NO 2

```
<211> LENGTH: 27
<212> TYPE: DNA
<213> ORGANISM: Rhabdovirus sp.

<400> SEQUENCE: 2
tctgtattat gggtttgatc agctaag                                              27

<210> SEQ ID NO 3
<211> LENGTH: 18
<212> TYPE: DNA
<213> ORGANISM: Rhabdovirus sp.

<400> SEQUENCE: 3
ctcgctgctg agcggttt                                                        18

<210> SEQ ID NO 4
<211> LENGTH: 18
<212> TYPE: DNA
<213> ORGANISM: Rhabdovirus sp.

<400> SEQUENCE: 4
aggattggag aattatac                                                        18
```